United States Patent
Nguyen et al.

(10) Patent No.: US 12,187,760 B2
(45) Date of Patent: Jan. 7, 2025

(54) PHOTON GENERATING SUBSTRATES FOR OLIGONUCLEOTIDE SYNTHESIS

(71) Applicant: MICROSOFT TECHNOLOGY LICENSING, LLC, Redmond, WA (US)

(72) Inventors: Bichlien Hoang Nguyen, Seattle, WA (US); Karin Strauss, Seattle, WA (US); Jake Allen Smith, Seattle, WA (US); Richard Prescott Rouse, Redmond, WA (US); Douglas Mitchell Carmean, Seattle, WA (US); Matthew David Turner, Carnation, WA (US); Gagan Gupta, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 124 days.

(21) Appl. No.: 17/331,321

(22) Filed: May 26, 2021

(65) Prior Publication Data
US 2022/0380403 A1    Dec. 1, 2022

(51) Int. Cl.
*C07H 21/04* (2006.01)
*B01J 19/00* (2006.01)
*B01J 19/12* (2006.01)

(52) U.S. Cl.
CPC .......... *C07H 21/04* (2013.01); *B01J 19/0046* (2013.01); *B01J 19/121* (2013.01);
(Continued)

(58) Field of Classification Search
CPC ........ C07H 21/04; C07H 1/00; B01J 19/0046; B01J 19/121; B01J 19/123;
(Continued)

(56) References Cited

U.S. PATENT DOCUMENTS 9,081,005 B2    7/2015   Kim
9,938,553 B2    4/2018   Jacobson
(Continued)

FOREIGN PATENT DOCUMENTS

CN    101104954 A    1/2008
CN    102628827 A    8/2012
(Continued)

OTHER PUBLICATIONS

McGall, et al., "High-density Oligonucleotide Probe Arrays", In Proceedings of Advances in Nucleic Acid and Protein Analyses, Manipulation, and Sequencing, vol. 3926, Mar. 22, 2000, pp. 106-110.

(Continued)

*Primary Examiner* — Xiuyu Tai
(74) *Attorney, Agent, or Firm* — Benjamin Keim; Newport IP LLC

(57) ABSTRACT

Photon generating substrates for light-directed oligonucleotide synthesis are disclosed. Light is generated within a solid-state stack that supports growing oligonucleotides. The light may be generated by microLEDs, a pass-through liquid crystal panel, or an LCoS system. Light passes through a transmissive layer on which growing oligonucleotides are attached. Patterning of the light is controlled by selective activation of the microLEDs or by selective control of the transparency of a liquid crystal layer. Photolabile blocking groups are selectively removed by exposure to patterned light emitted from the photon generating substrate.

20 Claims, 11 Drawing Sheets

(52) U.S. Cl.
CPC .... *B01J 19/123* (2013.01); *B01J 2219/00527* (2013.01); *B01J 2219/00711* (2013.01); *B01J 2219/00722* (2013.01); *B01J 2219/0879* (2013.01); *B01J 2219/1203* (2013.01)

(58) Field of Classification Search
CPC .... B01J 2219/00527; B01J 2219/00711; B01J 2219/00722; B01J 2219/0879; B01J 2219/1203; B01J 2219/00317; B01J 2219/00454; B01J 2219/00326; B01J 2219/00659; B01J 2219/00277; B01J 2219/00405; B01J 2219/00488; B01J 2219/00536; B01J 2219/0068; G06F 13/161; G06F 21/78; G06F 13/4234; G06F 2212/1052; G06F 2212/402; C12N 15/1027; C12N 15/1089; C12N 15/102; C12Q 1/6806; C12Q 2531/113; G11C 13/0019; Y02P 20/582; C40B 50/14; C40B 60/14; H01L 27/156; H01L 33/58; H01L 25/0753; H01L 33/56; H01L 33/0095; H01L 2933/005; H01L 24/95; H01L 2924/12041; H01L 2933/0058; H01L 2924/00012

See application file for complete search history.

(56) References Cited

U.S. PATENT DOCUMENTS

| | | | |
|---|---|---|---|
| 2007/0224091 A1* | 9/2007 | Okayama | C40B 60/14 422/131 |
| 2018/0030506 A1 | 2/2018 | Fujioka | |
| 2019/0165039 A1 | 5/2019 | Ku et al. | |
| 2019/0354871 A1 | 11/2019 | McFarland et al. | |
| 2019/0358604 A1* | 11/2019 | Nguyen | C07H 1/00 |
| 2020/0362397 A1 | 11/2020 | Zhou et al. | |
| 2023/0083189 A1* | 3/2023 | Burgess | C40B 40/10 |

FOREIGN PATENT DOCUMENTS

| | | |
|---|---|---|
| EP | 3746553 A1 | 12/2020 |
| WO | 0053309 A1 | 9/2000 |
| WO | 2014064104 A1 | 5/2014 |
| WO | 2020076976 A1 | 4/2020 |
| WO | 2021167807 A1 | 8/2021 |
| WO | 2022010934 A2 | 1/2022 |

OTHER PUBLICATIONS

"International Search Report and Written Opinion Issued in PCT Application No. PCT/US22/027748", Mailed Date: Aug. 3, 2022, 11 Pages.

Wu, et al., "3'-O-Modified Nucleotides as Reversible Terminators for Pyrosequencing", In Proceedings of the National Academy of Sciences, vol. 104, Issue 42, Oct. 16, 2007, pp. 16462-16467.

Albert, et al., "Light-Directed 5'→3' Synthesis of Complex Oligonucleotide Microarrays", In Journal of Nucleic Acids Research, vol. 31, Issue 7, Apr. 1, 2003, 9 Pages.

Blair, et al., "A Scalable Method for Multiplex LED-Controlled Synthesis of DNA in Capillaries", In Journal of Nucleic Acids Research, vol. 34, Issue 16, Sep. 8, 2006, 8 Pages.

Bowers, et al., "Virtual Terminator Nucleotides for Next-Generation DNA Sequencing", In Journal of Nature Methods, vol. 6, Issue 8, Aug. 2009, 7 Pages.

Gao, et al., "A Flexible Light-Directed DNA Chip Synthesis Gated by Deprotection using Solution Photogenerated Acids", In Journal of Nucleic Acids Research, vol. 29, Issue 22, Nov. 15, 2001, pp. 4744-4750.

Gao, et al., "In Situ Synthesis of Oligonucleotide Microarrays", In Journal of Biopolymers: Original Research on Biomolecules, vol. 73, Issue 5, Mar. 10, 2004, pp. 579-596.

Huang, et al., "Mini-LED, Micro-LED and OLED Displays: Present Status and Future Perspectives", In Journal of Light: Science & Applications, vol. 9, Issue 1, Jun. 18, 2020, 16 Pages.

Kretschy, et al., "Next-Generation o-Nitrobenzyl Photolabile Groups for Light-Directed Chemistry and Microarray Synthesis", In Angewandte Chemie International Edition, vol. 54, Issue 29, Jul. 13, 2015, pp. 8555-8559.

Lee, et al., "Photon-Directed Multiplexed Enzymatic DNA Synthesis for Molecular Digital Data Storage", In Journal of Nature Communications, vol. 11, Issue 1, Oct. 16, 2020, 9 Pages.

Marquez, et al., "Special Issue on Liquid Crystal on Silicon Devices: Modeling and Advanced Spatial Light Modulation Applications", In Journal of Applied Sciences, vol. 9, Issue 15, Jul. 29, 2019, 4 Pages.

Mathews, et al., "3'-O-Caged 2'-Deoxynucleoside Triphosphates for Light-Mediated, Enzyme-Catalyzed, Template-Independent DNA Synthesis", In Journal of Current Protocols in Nucleic Acid Chemistry, vol. 71, Issue 1, Dec. 2017, 38 Pages.

Mathews, et al., "Photo-Cleavable Nucleotides for Primer Free Enzyme Mediated DNA Synthesis", In Journal of Organic & Biomolecular Chemistry, vol. 14, Issue 35, Aug. 9, 2016, pp. 8278-8288.

McKendry, et al., "Individually Addressable AllnGaN Micro-LED Arrays With CMOS Control and Subnanosecond Output Pulses", In Journal of IEEE Photonics Technology Letters, vol. 21, Issue 12, Jun. 15, 2009, pp. 811-813.

Meldrum, et al., "Kinetics and Mechanism of DNA Repair-Preparation, Purification and Some Properties of Caged Dideoxynucleoside Triphosphates", In Biochemical Journal, vol. 266, vol. 3, Mar. 15, 1990, pp. 885-890.

Palluk, et al., "De Novo DNA Synthesis Using Polymerase-Nucleotide Conjugates", In Journal of Nature Biotechnology, vol. 36, Issue 7, Aug. 1, 2018, 10 Pages.

Sack, et al., "Express Photolithographic DNA Microarray Synthesis with Optimized Chemistry and High-Efficiency Photolabile Groups", In Journal of Nanobiotechnology, vol. 14, Issue 1, Mar. 2, 2016, 13 Pages.

Srivannavit, Onnop, "Design, Fabrication and Modeling of Microreactor Arrays for Biochips and Discovery Research", A Dissertation Submitted in Partial Fulfillment of the Requirements for the Degree of Doctor of Philosophy (Chemical Engineering), 2002, 24 Pages.

"OP02220 LCOS—Product Brief", Retrieved From: https://en.sekorm.com/doc/2010588.html, Jan. 7, 2020, 2 Pages.

Office Action Received for European Application No. 22725616.1, mailed on Jan. 9, 2024, 3 pages.

* cited by examiner

PHOTON GENERATING SUBSTRATES FOR OLIGONUCLEOTIDE SYNTHESIS

BACKGROUND

Light-directed oligonucleotide synthesis has traditionally been performed using photolithography masks or maskless array technologies. The photolithographic method is based on the use of optical imaging systems to deliver light to the synthesis surface, where array layout and sequences are determined by selective removal of photocleavable protecting groups on the terminus of each oligonucleotide. Photomask technologies pattern light using a fixed set of unique masks, where the number of unique masks required is equal to 4× the length of oligonucleotides. Maskless array technologies use digital projectors and digital micromirror devices (DMD) to pattern light. This eliminates the need for a unique mask set for each batch of oligonucleotide synthesis.

One emerging use of synthetic oligonucleotides is storage of digital data. Deoxyribonucleic acid (DNA) provides a high storage density and, if maintained in proper conditions, may be stable for hundreds of years. Using DNA as a medium for data storage requires synthesis of a large number of oligonucleotides with specific sequences. Neither photolithography masks nor DMDs are well suited for producing large quantities of oligonucleotides with arbitrary sequences. Photolithography masks are too costly and time-consuming because new masks must be made for each batch of oligonucleotides. Although DMD systems are more flexible, they are mechanically complex, require precise aiming of light, and are sensitive to vibrations. Currently the smallest achievable pitch with DMD is about 16 µm. This makes it difficult to scale DMD systems.

Although light-directed oligonucleotide synthesis is a useful technique for synthesizing oligonucleotides, current devices for generating patterned light are impractical or inefficient for synthesizing large numbers of oligonucleotides. Additional techniques and devices for patterning light with small pitch sizes will be valuable for use in many applications including storage of digital data in oligonucleotides. This disclosure is made with respect to these and other considerations.

SUMMARY

This disclosure provides devices, methods, and systems for precisely delivering light to specific locations on the surface of solid substrates. One non-limiting application for the use of this patterned light is light-directed oligonucleotide synthesis. Instead of using a complex DMD that projects light onto a solid substrate, a photon generating substrate generates light from within a stack. The stack serves both as the substrate on which the oligonucleotides are anchored and the source of light. It may be implemented as a single solid-state stack. The light source may be a microLED array patterned by selective activation of individual microLEDs; one or more lamps, lasers, LEDs, or microLEDs that are patterned by a pass-through liquid crystal panel; or one or more lamps, lasers, LEDs, or microLEDs that are patterned by a liquid crystal on silicon (LCoS) system.

Display technology using microLEDs, pass-through liquid crystal panels, and LCoS systems are able to control light emission at feature sizes of a few microns and arbitrary wavelengths. However, it is believed that none of these systems have been previously adapted for light-directed oligonucleotide synthesis. The solid-state systems provided in this disclosure emit photons in close proximity to growing oligonucleotides thereby minimizing or eliminating the alignment and vibration issues found with DMDs. These systems can also achieve a smaller pitch than DMDs, may include no moving parts, and can be produced efficiently using established techniques for semiconductor and display device manufacturing.

A photon delivery system suitable for, but not limited to, use in delivering patterned light for the synthesis of oligonucleotides may be built as a stack of a solid-state device similar to an electronic circuit. The stack of the photon delivery system may include a transmissive layer that functions as a solid substrate on which oligonucleotides are attached. The transmissive layer may be formed from an optically transparent material such as silicon dioxide glass, quartz, or a plastic polymer. The oligonucleotides may be attached to the transmissive layer using linkers, silane chemistry, or functionalization of the surface of the transmissive layer.

In some implementations, the transmissive layer may be overlaid with a patterning layer. The patterning layer may create a pattern on the surface of the transmissive layer that limits the transmission of light. The pattern may be formed by micro-etching that creates topographical structures or by overlaying non-transparent material. Alternatively, the patterning layer may limit locations where oligonucleotides are able to attach to the transmissive layer. This creates discrete spots with clusters of oligonucleotides and buffer space without oligonucleotides between the spots.

A focusing layer may underlie the transmissive layer. The focusing layer serves to focus or modify the light before contacting the transmissive layer. The focusing layer may be a collimator that creates collimated light. In other implementations, the focusing layer may be a lens formed of glass or similar material. If the light source is an array of microLEDs, the focusing layer may be implemented as a plurality of microlenses each aligned with a single one of the microLEDs. The microlenses may be collimating lenses. Alternatively, the focusing layer may be implemented as a microchannel grid.

The light source is configured to emit light of a specified wavelength. The specific wavelength is a wavelength that removes blocking groups attached to nucleotides. For example, the wavelength may be between about 350 nm and about 430 nm. If the light source is implemented as one or more LEDs such as an array of microLEDs, the LEDs may be gallium nitride (GaN) LEDs that emit light at a wavelength of about 365 nm. Selective activation of individual microLEDs in the microLED array controls the pattern of light incident upon the transmissive layer.

Alternatively, the light source may be one or more lamps, lasers, LEDs, or microLEDs that deliver light to the transmissive layer through a pass-through liquid crystal panel or an LCoS system. The pass-through liquid crystal panel or liquid crystals in the LCoS system controls the patterning of light that contacts the transmissive layer. The LCoS system can also include one or more alignment layers adjacent to the liquid crystal panel. The LCoS system includes a beam splitter which may be implemented as a prism. There may also be a polarizer located between the light source and the beam splitter.

The photon delivery system additionally includes a circuitry layer. The circuitry layer controls activation of individual LEDs in a microLED array or transparency of the liquid crystal panel. The circuitry layer may be implemented as a CMOS (complementary metal-oxide-semiconductor)

layer. The circuitry layer may underlie the microLED array or reflective electrodes used in an LCoS system. The circuitry layer may respond to signals received from a control system that specifies both the timing of activating the light source and the patterning of light from the light source.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures are schematic representations and not necessarily drawn to scale.

DETAILED DESCRIPTION

Figure 1:
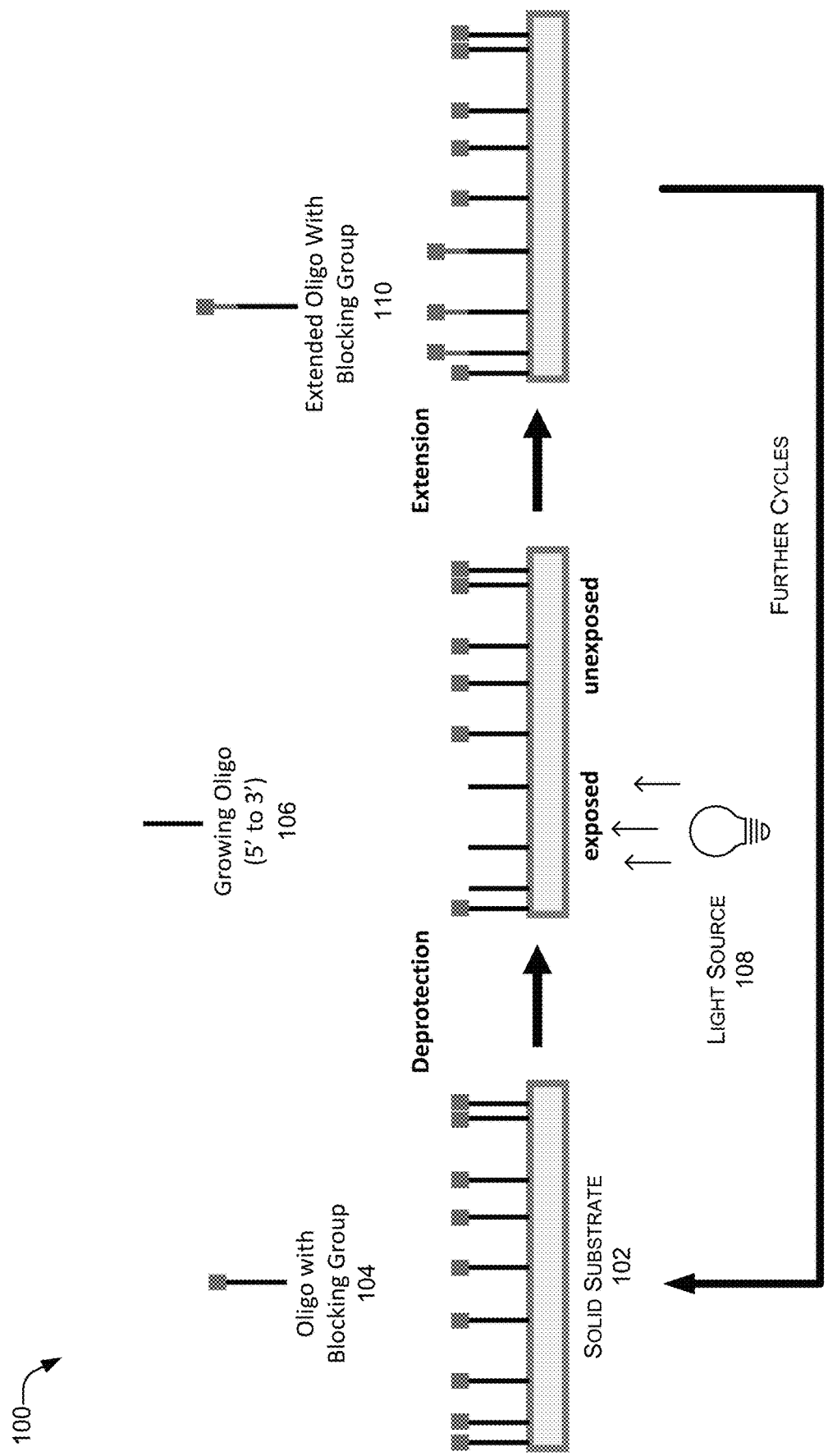
FIG. 1 is a diagram of light-directed oligonucleotide synthesis with light provided from beneath a solid substrate on which the oligonucleotides are attached.

This disclosure provides novel systems and methods for light-directed oligonucleotide synthesis. Photon delivery devices formed from stacks of solid-state material precisely deliver patterned light to a surface on which oligonucleotides or another polymer is synthesized. The light is generated from within the stacks by a microLED array or another light source. If a microLED array is used, patterning of the light is provided by selective activation of individual microLEDs. If another light source is used, the light is patterned by a pass-through liquid crystal panel or a LCoS system. The patterning of light is used to spatially control deblocking of the oligonucleotides or other polymer.

Patterned light generated by DMD has been used in various ways for oligonucleotide synthesis. Gao et al., A flexible light-directed DNA chip synthesis gated by deprotection using solution photogenerated acids, *Nucleic Acids Research*, Vol. 29(22), 4744-4750 (2001), Sack et al., Express photolithographic DNA microarray synthesis with optimized chemistry and high-efficiency photolabile groups, *J. Nanobiotechnol.*, 14:14 (2016), and Albert et al., Light-directed 5'→3' synthesis of complex oligonucleotide microarrays, *Nucleic Acids Research*, Vol. 31(7), e35 (2003) all describe techniques for synthesizing DNA microarray plates using DMDs to selectively deprotect growing oligonucleotides. Lee et al., Photon-directed multiplexed enzymatic DNA synthesis for molecular digital data storage, *Nature Communications*, Vol. 11, 5246 (2020) describes a technique for controlling enzymatic DNA synthesis using Terminal deoxynucleotidyl Transferase (TdT) with patterned light generated by a DMD. U.S. patent application Ser. No. 17/086,055 filed on Oct. 30, 2020 with the title "Spatially Addressable Control of Polymerase Activity" also provides techniques for using light to control enzymatic synthesis of oligonucleotides.

Even though general techniques for light-directed oligonucleotide synthesis are well-established, systems that use DMD are not scalable to produce large quantities of oligonucleotide strands with arbitrary sequences as will be needed for digital data storage applications. Modifications of modern display technologies such as microLED and LCoS are used to create systems that precisely control the emission of light from a substrate that is suitable for synthesis of oligonucleotides. These systems are both simpler and may have smaller pitch sizes than DMD systems.

There are many uses for synthetic oligonucleotides having specified sequences such as basic research, medicine, and nanoengineering (e.g., DNA origami). One relatively recent application for oligonucleotides is digital data storage. DNA may be used to store digital information by designing a sequence of nucleotide bases that encodes the zeros and ones of the digital information. There are various techniques and encoding schemes known to those of skill in the art for using nucleotide bases to represent digital information. See Lee Organick et al., *Random Access in Large-Scale DNA Data Storage,* 36:3 Nat. Biotech. 243 (2018) and Melpomeni Dimpoulou et al., *Storing Digital Data Into DNA: A Comparative Study of Quaternary Code Construction*, ICASSP Barcelona, Spain (2020). Advantages of using oligonucleotides rather than another storage media for storing digital information include information density and longevity. The sequence of nucleotide bases is designed on a computer and then oligonucleotides with those sequences are synthesized. The oligonucleotides may be stored and later read by an oligonucleotide sequencer to retrieve the digital information.

Oligonucleotides, also referred to as polynucleotides, include both DNA, ribonucleic acid (RNA), and hybrids containing mixtures of DNA and RNA. DNA includes nucleotides with one of the four natural bases cytosine (C), guanine (G), adenine (A), or thymine (T) as well as unnatural bases, noncanonical bases, and modified bases. RNA includes nucleotides with one of the four natural bases cytosine, guanine, adenine, or uracil (U) as well as unnatural bases, noncanonical bases, and modified bases. Nucleotides include both deoxyribonucleotides and ribonucleotides covalently linked to one or more phosphate groups.

Although the primary example provided in this disclosure is synthesis of oligonucleotides, the photon generating structures disclosed herein have uses in other applications. For example, they may be used for photoinitiated polymer synthesis of polymers other than oligonucleotides. In one technique, a photon initiator is used to generate radicals that initiate polymerization or that activate a photo redox catalyst. Additionally, the ability to create patterned light from within a stack may be used in various types of analyte/reporter systems such as by selectively exciting fluorophores.

Detail of procedures and techniques not explicitly described or other processes disclosed of this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, $4^{th}$ ed. (2012).

FIG. 1 is a diagram 100 showing a solid substrate 102 that is coated with a plurality of oligonucleotides capped with blocking groups 104. The solid substrate 102 may be surface functionalized to provide for attachment of oligonucleotides. The solid substrate 102 may be optically transparent. The solid substrate may be formed from silicon dioxide glass, quartz, a plastic polymer, or other material known to those of skill in the art for use as a substrate in solid-phase oligonucleotide synthesis.

The solid substrate 102 is an example of a platform used for solid-phase synthesis. Solid-phase synthesis is a method in which molecules are covalently bound on a solid support material and synthesized step-by-step in a single reaction vessel. Solid-phase synthesis may be used to make many types of polymers including, but not limited to, oligonucleotides 106.

The 5' ends of the growing oligonucleotides 106 are attached to the solid substrate 102. The oligonucleotides 106 may be attached to the solid substrate 102 by any one of numerous techniques known to those of ordinary skill in the art for attaching oligonucleotides to a solid surface. Suitable techniques include those used in conventional solid-phase synthesis of oligonucleotides and for the creation of DNA microarrays. For example, oligonucleotides 106 may be attached directly to a solid substrate 102 formed from silicon dioxide glass. One suitable technique for functionalizing glass surfaces is described in Sack et al., Express photolithographic DNA microarray synthesis with optimized chemistry and high-efficiency photolabile groups, *J. Nanobiotechnol.*, 14:14 (2016).

In some implementations, the surface of the solid substrate 102 may be functionalized and the oligonucleotides 106 may be attached to the functional groups rather than directly to the molecules of the solid substrate 102. In implementations, the surface of the solid substrate 102 may be silanized and the oligonucleotides 106 attached with silane chemistry. If the solid substrate 102 is formed from plastic polymer, the polymer may be functionalized to provide points of attachment for the oligonucleotides 106. Alternatively, the oligonucleotides 106 may be attached via a cleavable or non-cleavable linker. If the linker is not cleavable, a template oligonucleotide can be hybridized to an anchor strand. If attached via cleavable linkers, the linker chemistry may be photochemical acid/base, or redox activated. Example techniques for attaching oligonucleotides to solid substrates using spaces and linkers are provided in Xiaolian Gao et al., In Situ Synthesis of Oligonucleotide Microarrays, *Biopolymers*, Vol. 73, 579-596 (2004).

The blocking groups 104 on the ends of the oligonucleotides 106 prevent extension of the oligonucleotides 106 by a polymerase. The blocking groups 104 may be located on the 3'-end of the oligonucleotides 106. Removal of a 3' blocking group 104 replaces the blocking group 104 with a 3' hydroxyl group. Any type of known or later developed photolabile blocking group 104 may be used.

Photolabile blocking groups are removed by exposure to a specific wavelength of light. There are a large number of known types of photo-cleavable linkers that can be used to attach blocking groups 104 which are not themselves photolabile. Common classes of photolabile linkers include nitrobenzyl-based linkers, benzyl nitrile-based linkers, benzyl-based linkers, and carbonyl-based linkers. Amine-to-thiol cross-linkers are also photolabile and may be lengthened by attachment to a polyethylene glycol (PEG) chain. Amine-to-thiol bonds may be cleaved by ultraviolet (UV) light with a wavelength of about 365-405 nm. One example of a photocleavable blocking group is the "virtual terminator" described in Jayson Bowers et al., Virtual terminator nucleotides for next-generation DNA sequencing, 6(8) *Nat. Methods* 593 (2009).

Each species of nucleotide may be combined with a different photolabile blocking groups that is removed by a different wavelength of light. For example, nucleotides that contain adenine (A) may have blocking groups that are cleaved with 365 nm light, nucleotides that contain guanine (G) may have blocking groups that are cleaved with 375 nm light, nucleotides that contain cytosine (C) may have blocking groups that are cleaved with 385 nm light, and nucleotides that contain thymine (T) or uracil (U) may have blocking groups that are cleaved with 395 nm light. Using different blocking groups combined with different light sources may provide more slight control over which nucleotide is unblocked. This may reduce the number synthesis errors that arise from incorporating a nucleotide on the wrong oligonucleotide.

During a deprotection step, a light source 108 provides photons that remove blocking groups 104 at the locations on the surface of the solid substrate 102 exposed to the light. To enact controlled extension of the growing oligonucleotides 106, the blocking groups 104 are first removed from a spatially clustered portion of the population by exposure to light at a wavelength that causes removal of the blocking groups 104. The blocking groups 104 remain attached in the areas of the solid substrate 102 that are not exposed to the light source 108. The light source 108 may come from within a stack and shine through the solid substrate 102 illuminating the oligonucleotides 106 from below. Alternatively, the light source 108 may shine from above (not shown in FIG. 1) and thus light will contact the surface of the solid substrate 102 without passing through the solid substrate 102. The solid substrate 102 does not need to be optically transparent if the light source 108 is located above the solid substrate 102.

Photolabile blocking groups 104 and techniques for light-directed oligonucleotides synthesis are known to those of ordinary skill in the art. The photolabile blocking groups 104 may include a nitrobenzyl group, a (2-nitrophenyl)acetyl group, or a trityl group removed by a photogenerated acid. Thus, the photolabile out blocking groups 104 may be directly removed by exposure to photons of an appropriate wavelength or may be removed by localized generation of a photo-generated acid. Thus, as used herein, photolabile blocking groups 104 includes blocking groups that are themselves removed by exposure to light, blocking groups attached to a photolabile linker, and acid-cleavable blocking groups cleaved by a photogenerated acid.

In an implementation, the blocking groups 104 may be benzoyl-2-(2-nitrophenyl)propoxycarbonyl (Bz-NPPOC) or thiophenyl-2-(2-nitrophenyl)propoxycarbonyl (SPh-NPPOC). See Kretschy et al., Next-Generation o-Nitrobenzyl Photolabile Groups for Light-Directed Chemistry and Microarray Synthesis, *Angew. Chem. Int. Ed., Vol.* 54, 8555-8559, (2015).

In an implementation, the blocking groups 104 may be photolabile 5'-phosophoramidites [3'-NPPOC-deoxyadenosine (N6-benzoyl)-5'-β-cyanoethylphosphoramidite, 3'NPPOC-deoxycytidine (N4-acetyl)-5'-β-cyanoethylphosphoramidite, 3'-NPPOC-deoxyguanosine (N2-dimethylformamidine)-5'-b-cyanoethylphosphoramidite and 3'-NPPOCdeoxythymidine-5'-β-cyanoethylphosphoramidite] and of 3'-Phosphoramidites [5'-NPPOC-deoxyadenosine (N6-tac)-3'-β-cyanoethylphosphoramidite, 5'-NPPOCdeoxycytidine (N4-isobutyryl)-3'-β-cyanoethylphosphoramidite, 5'-NPPOC-deoxyguanosine (N2-ipac)-3'-β-cyanoethylphosphoramidite or 5'-NPPOC-deoxythymidine-3'-β-cyanoethylphosphoramidite]. See Albert et al., Light-directed 5'→3' synthesis of complex oligonucleotide microarrays, *Nucleic Acids Research*, Vol. 31(7), e35 (2003).

In an implementation, the blocking groups 104 may be 5'-(α-methyl-2-nitropiperonyl) oxycarbonyl (MeNPOC), dimethoxybenzoincarbonate (DMBOC), 2-(2-nitrophenyl) propoxycarbonyl (NPPOC), or thiophenyl-2-(2-nitrophenyl)-propoxycarbonyl (SPh-NPPOC). See Sack et al., Express photolithographic DNA microarray synthesis with optimized chemistry and high-efficiency photolabile groups, *J. Nanobiotechnol.*, 14:14 (2016).

In an implementation, the nucleotides that include blocking groups 104 may be 3'-O-(2-nitrobenzyl)-2'-deoxyribonucleoside triphosphates or 3'-O-(4,5-dimethoxy-2-nitrobenzyl)-2'-deoxyribonucleoside triphosphates. See Mathews et al., Photo-cleavable nucleotides for primer free enzyme mediated DNA synthesis, *Organic & Biomolecular Chemistry*, Vol. 14, 8278-8288 (2016).

In an implementation, the blocking groups 104 may be 3'-O-(2-nitrobenzyl)-2'deoxy ribonucleoside triphosphates (NB-dNTPs) or 3'-O-(4,5-dimethoxy2-nitrobenzyl)-2'-deoxy ribonucleoside triphosphates (DMNB-dNTPs). See Mathews et al., 3'-O-Caged 2'-deoxynucleoside triphosphates for light-mediated, enzyme-catalyzed, template-independent DNA synthesis. *Current Protocols in Nucleic Acid Chemistry*, Vol. 71, 13.17.1-13.17.38 (2017). Use of 3'-O-(2-nitrobenzyl)-dNTPs as a photocleavable blocking group is also described in Wu et al., 3'-O-modified nucleotides as reversible terminators for pyrosequencing, *PNAS*, Vol. 104 (42), 16462-16467 (2007).

In an implementation, the nucleotides with blocking groups 104 may be [α-1-(2-nitrophenyl)ethyl ester] dideoxynucleoside triphosphates. See Meldrum et al., Kinetics and mechanism of DNA repair, *Biochem. J*, Vol. 266, 885-890 (1990). Other types of photolabile blocking groups 104 besides those explicitly mentioned here are also contemplated.

Following removal of the blocking groups 104, the entire surface of the solid substrate 102 may be flooded or covered with nucleotides containing a blocking group. These blocked nucleotides are incorporated to the ends of the unblocked oligonucleotides 106 so as to extend and re-block those strands. A nucleotide is a nucleoside linked to one or more phosphate groups. In some implementations, the nucleotide may be a deoxynucleoside triphosphate (dNTP) or a ribose triphosphate (NTP).

The nucleotides may be limited to only a single species of nucleotide (e.g., only A, G, C, or U/T) so that the same nucleotide is added to all of the extended oligonucleotides with blocking groups 110. Depending on the structure of the nucleotide and/or the reaction conditions, the nucleotide incorporates once or multiple times at locations on the solid substrate 102 which were exposed to light. The free nucleotides are incorporated onto the ends of the growing oligonucleotides 106 using conventional techniques for de novo oligonucleotide synthesis such as phosphoramidite chemistry or enzymatic synthesis.

Nucleotides and other entities that are not attached to the oligonucleotides 106 or the solid substrate 102 are present in a solution (not shown) that covers the surface of the solid substrate 102. The solution may include buffers, salts, electrolytes, and the like. Further cycles of deprotection and extension allow for the synthesis of oligonucleotides 106 with arbitrary sequences. Nucleotides that remain in solution may be removed by a wash step between cycles.

Figure 2:
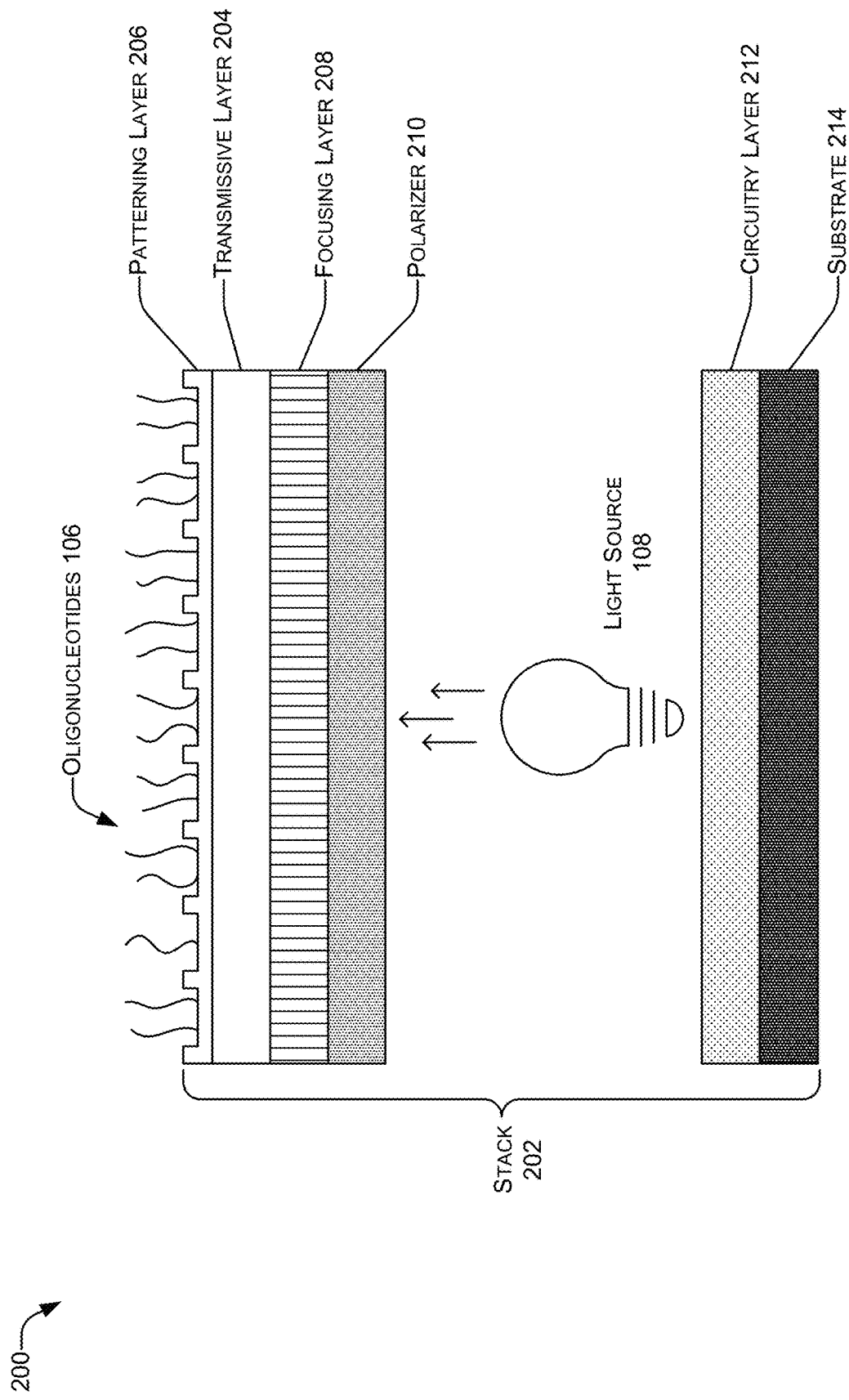
FIG. 2 is a schematic of a photon delivery system formed from a single solid-state stack.

FIG. 2 is a schematic illustration 200 of a photon delivery system formed from a single stack 202 comprising multiple layers. In an implementation, the stack 202 may be a solid-state stack that includes semiconductor devices such as transistors, diodes, and integrated circuits (ICs). In some implementations, a solid-state stack may not include moving parts. The stack 202 includes a light source 108. The light source 108 may be a microLED array, one or more LEDs, a lamp, or a laser. Specific examples of implementations using particular light sources 108 are provided below. In some implementations, the photon delivery system may include multiple light sources 108 that each generate light at different wavelengths.

The wavelength of light emitted by the light source 108 may be tuned to a wavelength that cleaves or removes photolabile blocking groups by various layers in the stack 202. The specific wavelength will depend on the chemistry of the photolabile structure. In some implementations, the wavelength may be between 350-430 nm. For example, the wavelength may be about 365 nm. In some implementations, a low pass cutoff implemented by a filter or other technique known to those of ordinary skill in the art may block transmission of light at a wavelength of less than 350 nm. Light with a wavelength lower than 350 nm such as far UV light may cause damage to oligonucleotides. Thus, due to filtering or tuning of the light, the specific range of wavelengths that reaches the oligonucleotides 106 may be different than the wavelength of light generated by the light source 108.

Oligonucleotides 106 may be attached to a transmissive layer 204 at or near the surface of the stack 202. The transmissive layer 204 is an optically transparent layer formed from materials such as silicon dioxide glass, quartz, or plastic polymer. Techniques for attaching oligonucleotides 106 to a solid substrate are described above and known to those of ordinary skill in the art. The transmissive layer 204 is impervious to fluids and is exposed to buffers and other solutions used for the synthesis of oligonucleotides 106. The stack 202 itself may be placed in a jig which holds the stack 202 seals the surface of the stack 202 so that the lower layers are not exposed to fluids.

The stack 202 may optionally include a patterning layer 206. The patterning layer 206 may be placed over the transmissive layer 204. The patterning layer 206 creates a pattern on the surface of the stack 202 that either limits transmission of light or limits locations for attachment of the oligonucleotides 106. The pattern created by the patterning layer 206 may assist with prevention of crosstalk between different synthesis sites by providing spatial confinement.

In implementations in which the patterning layer 206 limits transmission of light, the patterning layer 206 may comprise topographical structures such as wells or tunnels. The patterning layer 206 may be formed from an optically opaque material such that light from the light source 108 only passes through selected regions of the patterning layer 206 in which no structure is present (e.g., holes). Thus, deblocking and oligonucleotide synthesis will only occur at those locations on the surface of the stack 202 which light is allowed through by the patterning layer 206.

In implementations in which the patterning layer 206 limits the attachment of oligonucleotides 106, there will be spots on the surface of the transmissive layer 204 where oligonucleotides 106 are present surrounded by buffer regions where there are no oligonucleotides 106. Oligonucleotide attachment may be patterned by chemical techniques that treat the service of the transmissive layer 204 in such a way that prevents oligonucleotide 106 attachment. For example, patterning may be achieved by selectively functionalizing only discrete spots on the surface of the transmissive layer 204. Oligonucleotides 106 can attach to the functionalized regions on the surface of the transmissive layer 204 but will not attach to other portions of the transmissive layer 204. A pattern of microstructures can also be created by the patterns layer 206 that prevents attachment of oligonucleotides 106.

An optional focusing layer 208 is configured to direct the light from the light source 108 onto the transmissive layer 204. The focusing layer 208 modify, focus or adjust a characteristic of the light before it reaches the transmissive layer 204. The focusing layer 208 may be implemented as focusing optics such as a lens that focused light from the light source 108 onto the surface of the transmissive layer 204. The lens may be made of glass or any suitable material conventionally used for lenses. The focusing layer 208 may also be implemented as a microchannel grid. A microchannel grid may be used if the light source 108 is separated from the transmissive layer 204 by some distance. In implementations in which the light source 108 is a microLED array, the focusing layer 208 may be an array of microlenses each aligned with a corresponding one of the microLEDs. For example, each microlens may be approximately 2 µm in diameter. In some implementations, the focusing layer 208 may be a collimator. A collimated beam of light has parallel rays and therefore will spread minimally as it propagates. This may improve the precision and lead to smaller pitch sizes. If microlenses are used together with a microLED array, each microlens may be a collimating microlens.

The stack 202 may also include one or more polarizers 210. A polarizer is an optical filter that lets light waves of a specific polarization pass through while blocking light waves of other polarizations. It can filter a beam of light of undefined or mixed polarization into a beam of well-defined polarization, that is polarized light.

The stack 202 also includes a circuitry layer 212. The circuitry layer 212 receives instructions as electrical signals and controls the pattern of illumination generated by the photon delivery device. The circuitry layer 212 provides digital control over which portions of the stack 202 emit light. The circuitry layer 212 may be implemented with complementary metal-oxide-semiconductor (CMOS) technology. CMOS may include metal-oxide-semiconductor field-effect transistors (MOSFETs) made through a triple-well process or by a silicon-on-insulator (SOI) process. A series of controllable gates/transistors implemented with CMOS circuits can be controlled to pattern the light generated by the light source 108.

The stack 202 may be built upon a substrate 214 such as any substrate conventionally used in the fabrication of electronic circuits. For example, the substrate 214 may be a printed circuit board (PCB) or a bare wafer.

Figure 3:
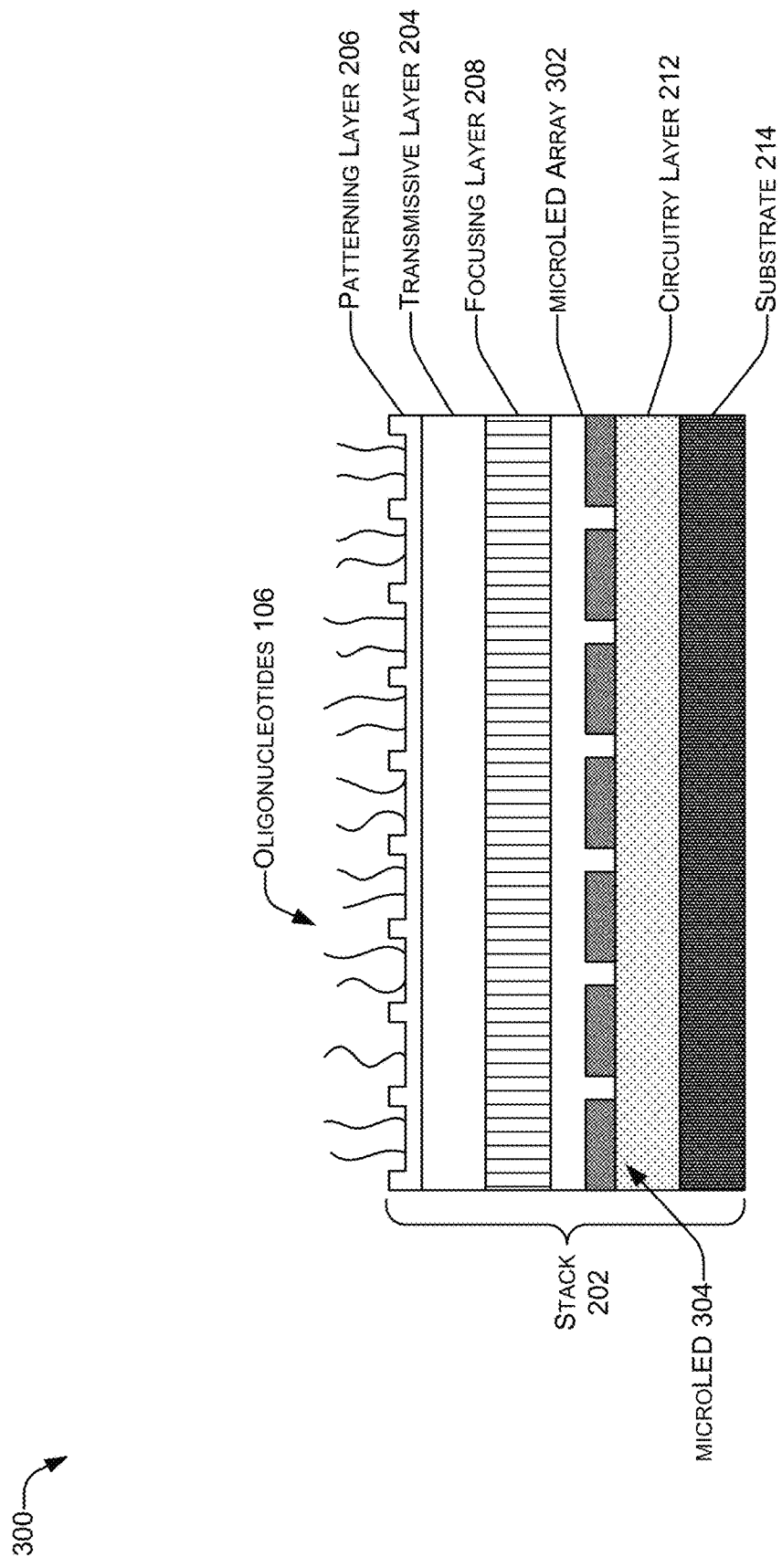
FIG. 3. is a schematic of a photon delivery system that includes a microLED array.

FIG. 3 is a schematic illustration 300 of a photon delivery system implemented with a microLED array 302. Other layers of the photon delivery system may be the same or similar to those described in FIG. 2. The microLED array 302 consists of an array of microscopic LEDs 304 forming individually-addressable elements. The microLED array 302 may be the same or similar as microLED arrays used in display devices. MicroLED displays consist of arrays of microscopic LEDs forming the individual pixel elements. Each LED 304 can be as small as 5 µm across. Individual pixels are turned on or off. Flux of the microLED array may be readily tuned. Each pixel is a diode. MicroLED displays are discussed generally in Huang et al., Mini-LED, Micro-LED and OLED displays: present status and future perspectives, *Light: Science & Applications*, Vol. 9:105 (2020).

The microLED array 302 may be driven via a hybrid CMOS and integrated circuit (IC) hybrid assembly in the circuitry layer 212. In an implementation, a memory programmed CMOS circuit may be used to control individual memory cells. Memory cells each have a position representing a single microLED. Programming drives a Mosfet circuit with appropriate additional components to deliver the current in a controlled fashion to the microLEDs.

The microLED array 302 may be implemented with or without a separate driver circuit. Each microLED may be integrated into a separate memory cell specific to that single microLED. Thus, the microLED array 302 may be combined with the circuitry layer 212 into a single layer in which the LEDs and current control circuit are integrated into a memory cell for each of the individual microLEDs. Alternatively, fewer that one memory cell per LED may be used, however that will reduce the level of addressability of the microLED array. McKendry et al., Individually Addressable AlInGaN Micro-LED Arrays With CMOS Control and Sub-nanosecond Output Pulses, *IEEE Photonics Technology Letters*, Vol. 21(12), 1041-1135 (2009) describes a microLED array in a flip-chip format that is compatible with CMOS control electronics.

Various LEDs that generate light at specific wavelengths are known to those of ordinary skill in the art. The appropriate type of LED based on the required wavelength may be selected. In implementation, the LEDs of the microLED array may generate ultraviolet light with a wavelength of about 365-370 nm. Ultraviolet light may be generated by a Gallium Nitride blue LED. One example of a suitable LED is the AlInGaN-based micro-light-emitting diode described in McKendry et al. Another type of suitable LED is the Roithner, UVLED365-10 described in Blair et al., A scalable method for multiplex LED-controlled synthesis of DNA in capillaries, *Nucleic Acids Research*, Vol. 34(16), e110, (2006).

Figure 4:
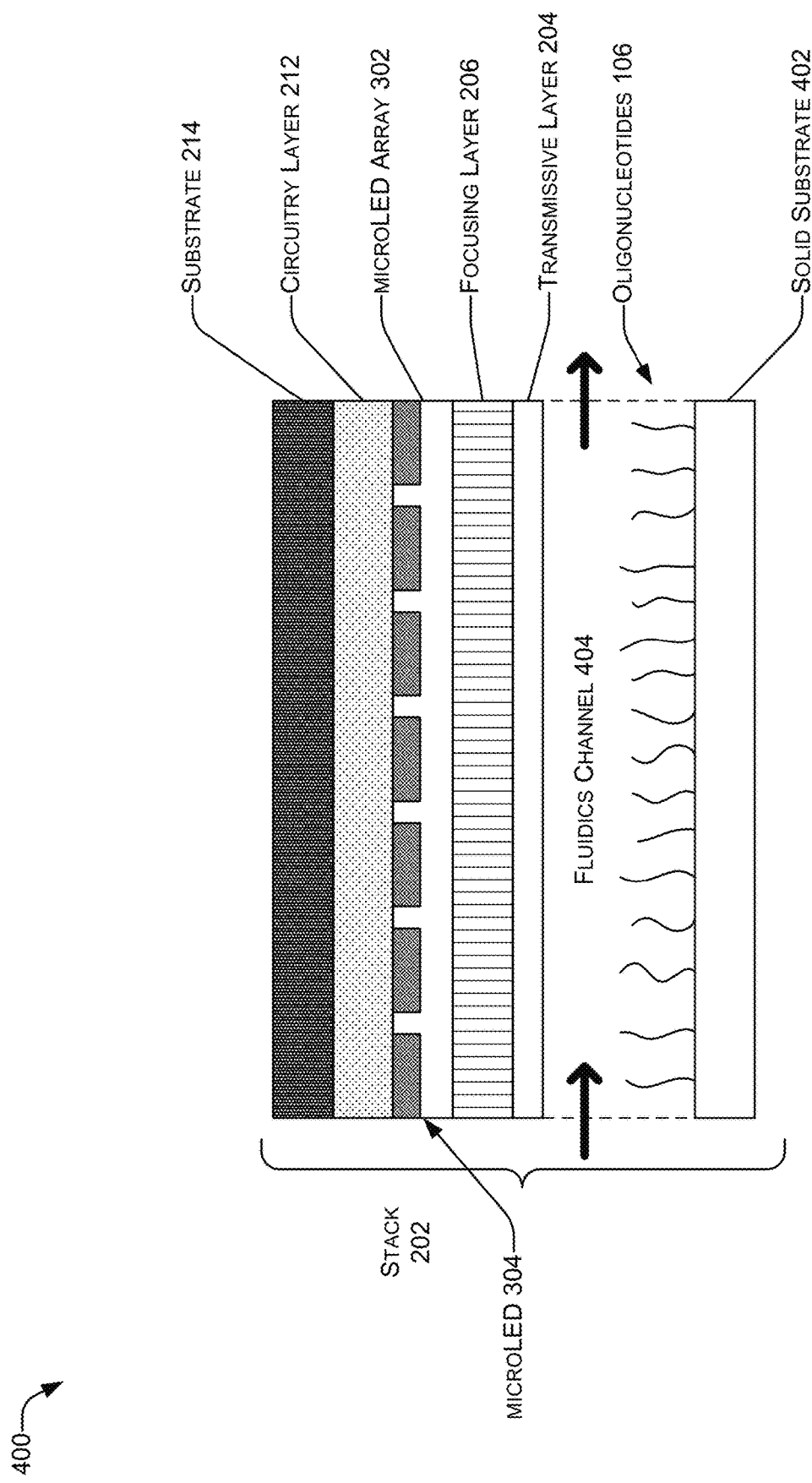
FIG. 4 is a schematic of a photon delivery system in which there is a fluidics channel between a solid substrate anchoring oligonucleotides and a light source.

FIG. 4 is a schematic illustration 400 of a photon delivery system in which a microLED array 302 is positioned above a solid substrate 402. Other layers of the photon delivery system may be the same or similar to those described in FIG. 2 or 3. In this implementation, instead of shining up through the solid substrate 402, light shines down onto the surface of the solid substrate 402 that is coated with a plurality of oligonucleotides 106. The solid substrate 402 may or may not be optically transparent. Thus, in this alternative configuration of a stack, the patterned light is still generated from within the photon generating substrate but projected across the fluidic channel to contact the oligonucleotides 106. A patterning layer 206, although not shown in this illustration, may be present either beneath the transmissive layer 204 to limit transmission of light or on the surface of the solid substrate 402 limit locations where the oligonucleotide is 106 may attach the solid substrate 402.

The fluidic channel 404 may be implemented as a tube, pipe, conduit, or passageway going through the stack 202. The fluidic channel 404 is configured to carry fluids used for oligonucleotide synthesis such as buffers across the surface of the solid substrate 402. The transmissive layer 204 provides a barrier impervious to fluids that prevents the contents of the fluidic channel 404 from contacting other layers of the stack 202. The distance between the transmissive layer 204 and the surface of the solid substrate 402 may be small to minimize diffusion of the light before it contacts the oligonucleotides 106.

Figure 5:
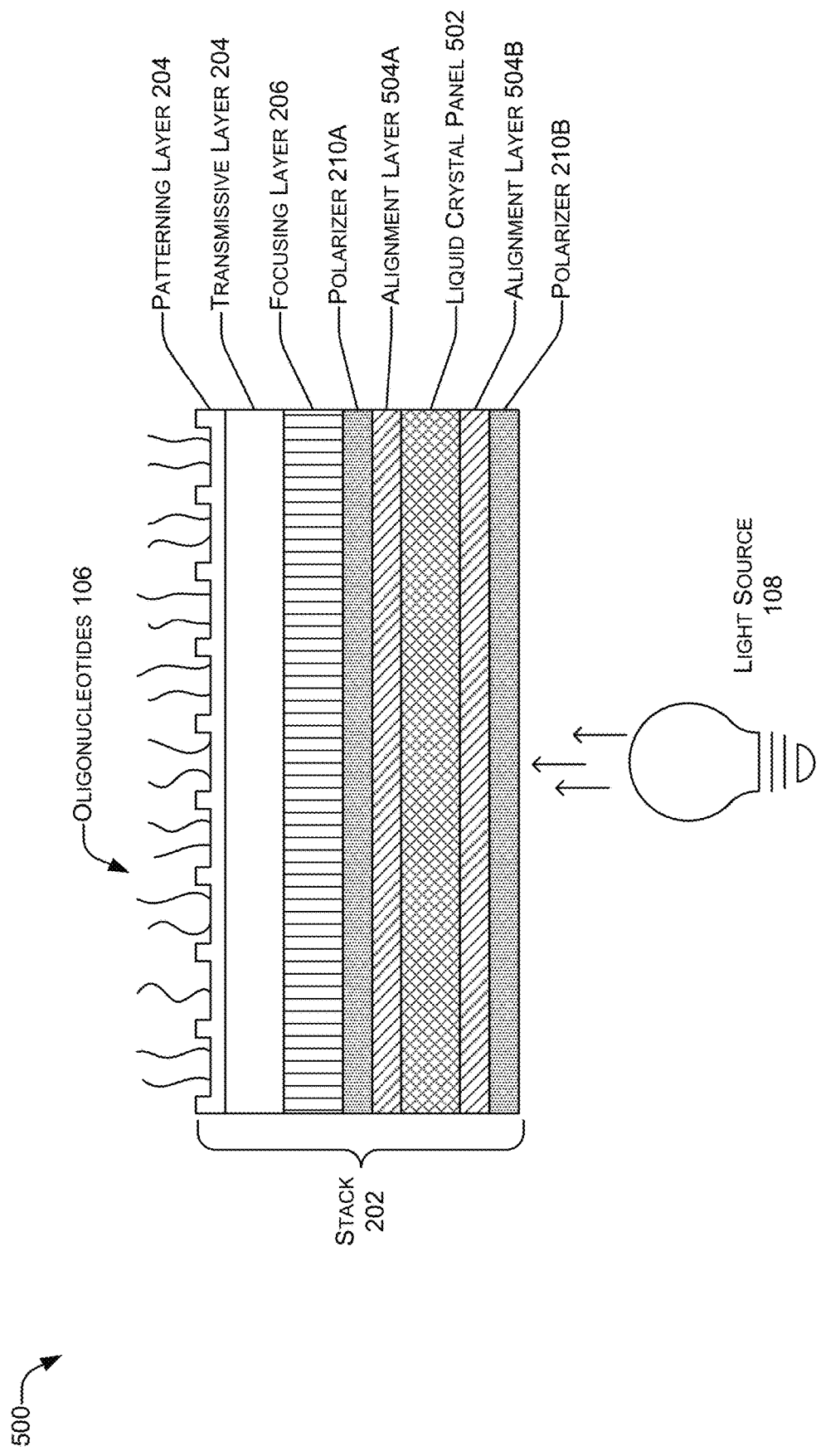
FIG. 5 is a schematic of a photon delivery system that includes a pass-through liquid crystal panel.

FIG. 5 is a schematic illustration 500 a photon delivery system in which a liquid crystal panel 502 is used in a pass-through configuration to pattern light emitted from a light source 108. Other layers of the photon delivery system may be the same or similar to those described in FIG. 2. The liquid crystal panel 502 changes opacity in response to voltage. This provides a very fine level of control for transmission of light such that pitch sizes below 4 μm are possible. The pass-through liquid crystal panel 502 may be placed between two alignment layers 504A, 504B and between two polarizers 210A, 210B.

The alignment layers 504A, 504B are used to orientate the liquid crystal molecules with a specific pretilt angle, which is the angle between the director of the liquid crystal molecules and the alignment layers. The pretilt angle is important to obtain a defect-free alignment and also to improve performance, such as response time. In some implementations, the alignment layers 504A, 504B are polyimide (PI) alignment layers used to align liquid crystal molecules nearly parallel and perpendicular to the substrates using homogeneous PI and homeotropic PI, respectively. The alignment mechanism depends on the morphology of PI alignment layers and intermolecular interactions between liquid crystal molecules and PI molecules.

In this implementation, light source 108 may be any light source capable of generating light of a suitable wavelength. For example, the light source 108 may be any type of lamp or LED used with LCD display systems. Alternatively, a microLED array may be used as the light source. However, in this implementation, patterning is provided by light passing through the liquid crystal panel 502 not by selective activation of individual microLEDs in the microLED array. The light source 108 may be a laser. There may be more than one light source 108 that each emit light at different wavelengths.

Figure 6:
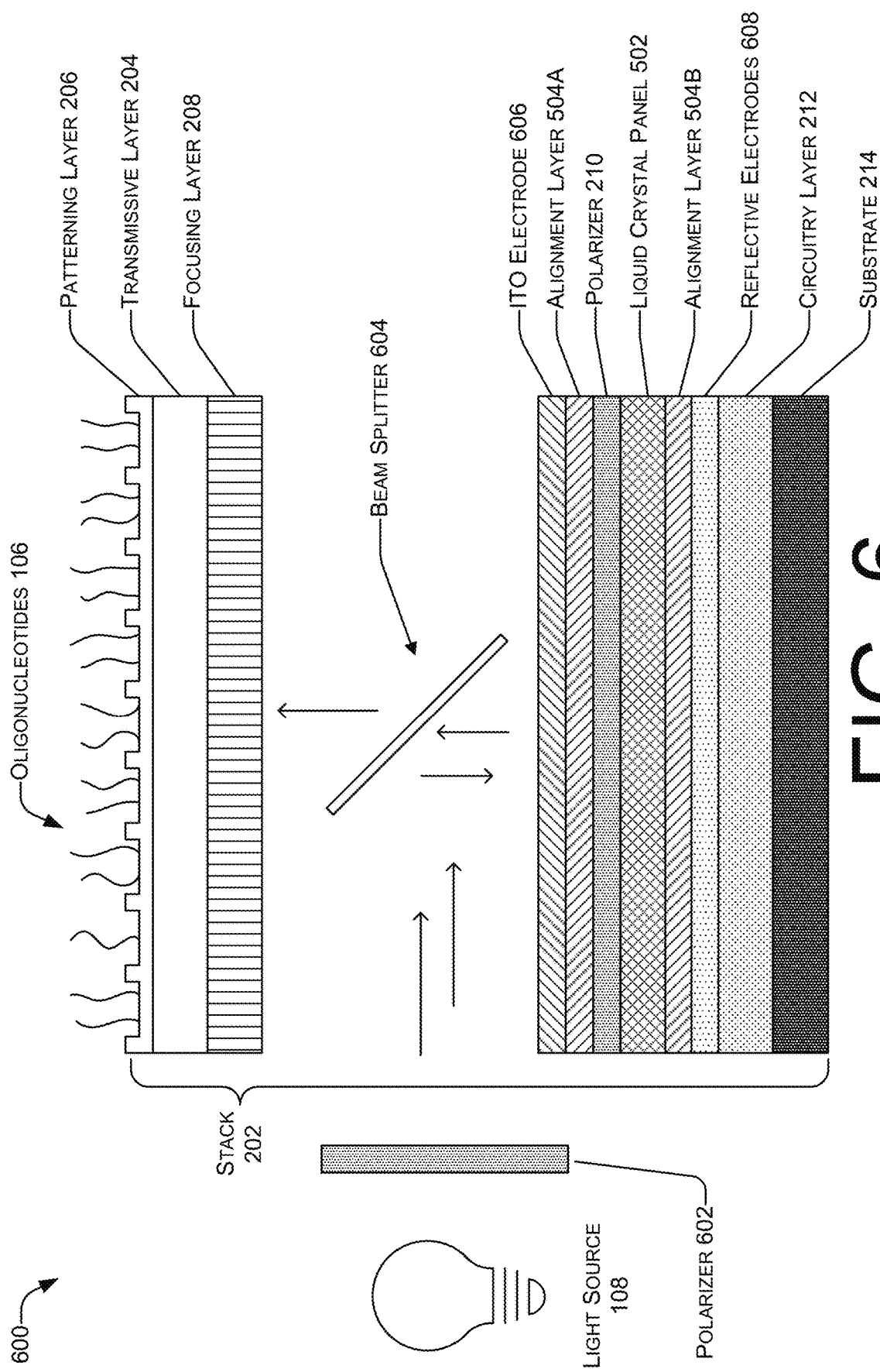
FIG. 6 is a schematic of a photon delivery system that includes a LCoS system.

FIG. 6 is a schematic illustration 600 of a photon delivery system that uses LCoS system to direct patterned light onto the transmissive layer 204. LCoS systems have been used in display devices to create reflective active-matrix liquid-crystal displays using a liquid crystal panel 502 on top of a silicon backplane. Liquid crystal on silicon (LCoS) devices may be composed of a high-performance silicon CMOS backplane, which controls the liquid crystal layer light modulating properties. LCoS systems used for display devices are discussed in Marquez and Lizana, Special Issue on Liquid Crystal on Silicon Devices: Modeling and Advanced Spatial Light Modulation Applications, *Appl. Sci.*, Vol. 9, 3049 (2019). The LCoS system may include a polarizer 602 between the light source 108 and a beam splitter 604. The beam splitter 604 may be implemented, for example, as a prism. In some implementations, the beam splitter 604 may itself be polarizing and the polarizer 602 may be omitted. The pitch size achieved with a LCoS system may be as small as 2.79 μm.

The LCoS system may include an indium tin oxide (ITO) electrode 606 between the beam splitter 604 and the liquid crystal panel 502. LCoS system also includes reflective electrodes 608 on the opposite side of the liquid crystal panel 502 as the transmissive layer 204. The reflective electrodes 608 may be formed from aluminum or aluminum alloy. As used herein, an LCoS system includes at least the light source 108, the beam splitter 604, liquid crystal panel 502, and reflective electrodes 608.

One example of an LCoS system that may be adapted for use in oligonucleotide synthesis is the OPO2220 LCoS available from OmniVision (Santa Clara, Calif.). The red, green, and blue LEDs used to generate light for a display device may be substituted with LEDs of the appropriate wavelength(s) (e.g., UV) for cleaving photolabile blocking groups.

Figure 7:
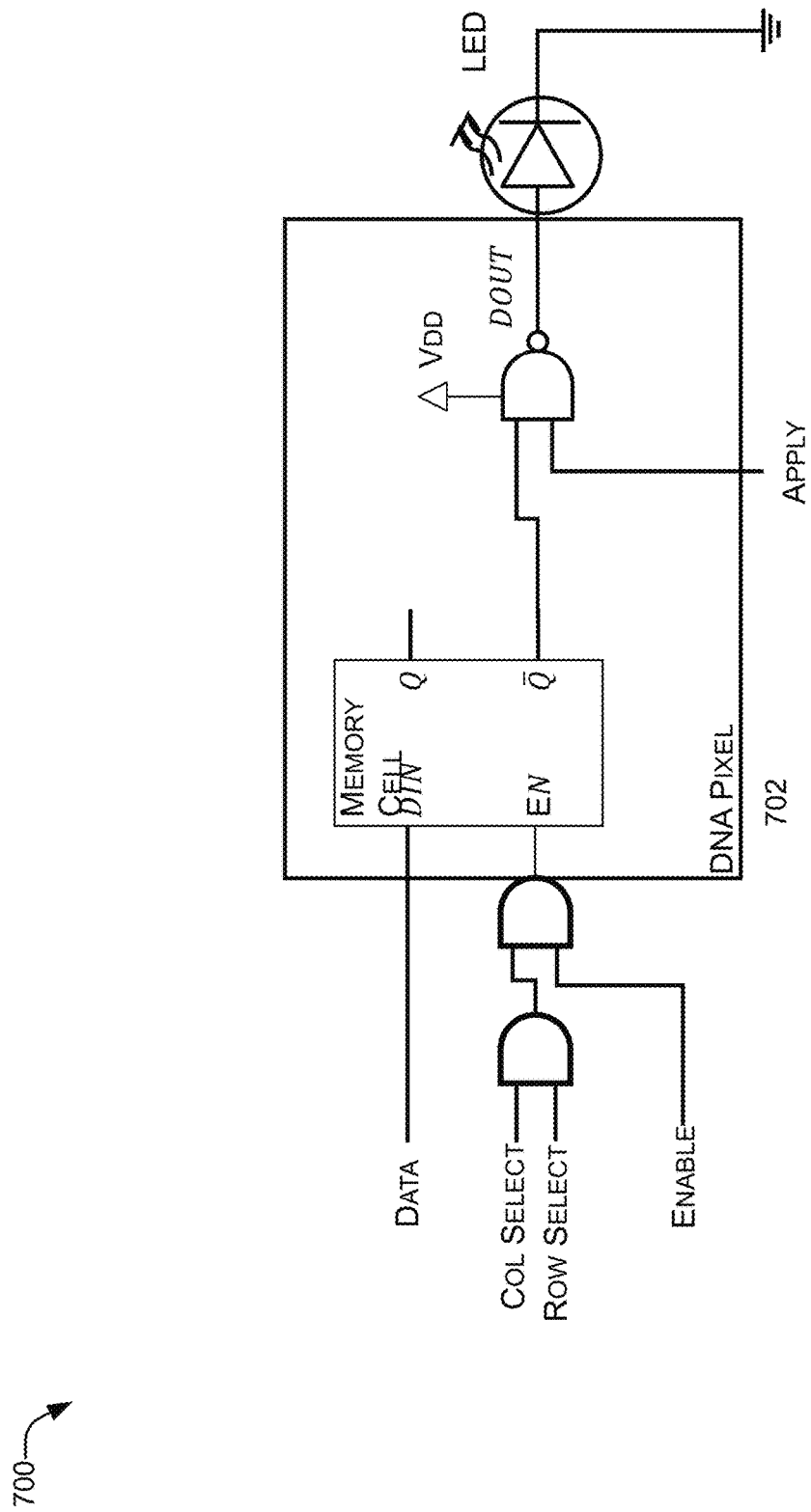
FIG. 7 is a circuitry diagram for controlling a LED in a photon delivery system.

FIG. 7 shows an illustrative circuitry diagram 700 that may be used to drive microLEDs in a microLED array. The circuitry includes a DNA pixel 702. The column select and row select inputs are used per-cell to select from the address decoder. The enable input is used for global enable to program memory. The memory cell may be implemented as flip-flop, static random-access memory (SRAM), or dynamic random-access memory (DRAM). The apply input is global enable to drive memory contents to drive LEDs. The voltage supply, VDD, is a voltage level shifter to drive an LED.

Figure 8:
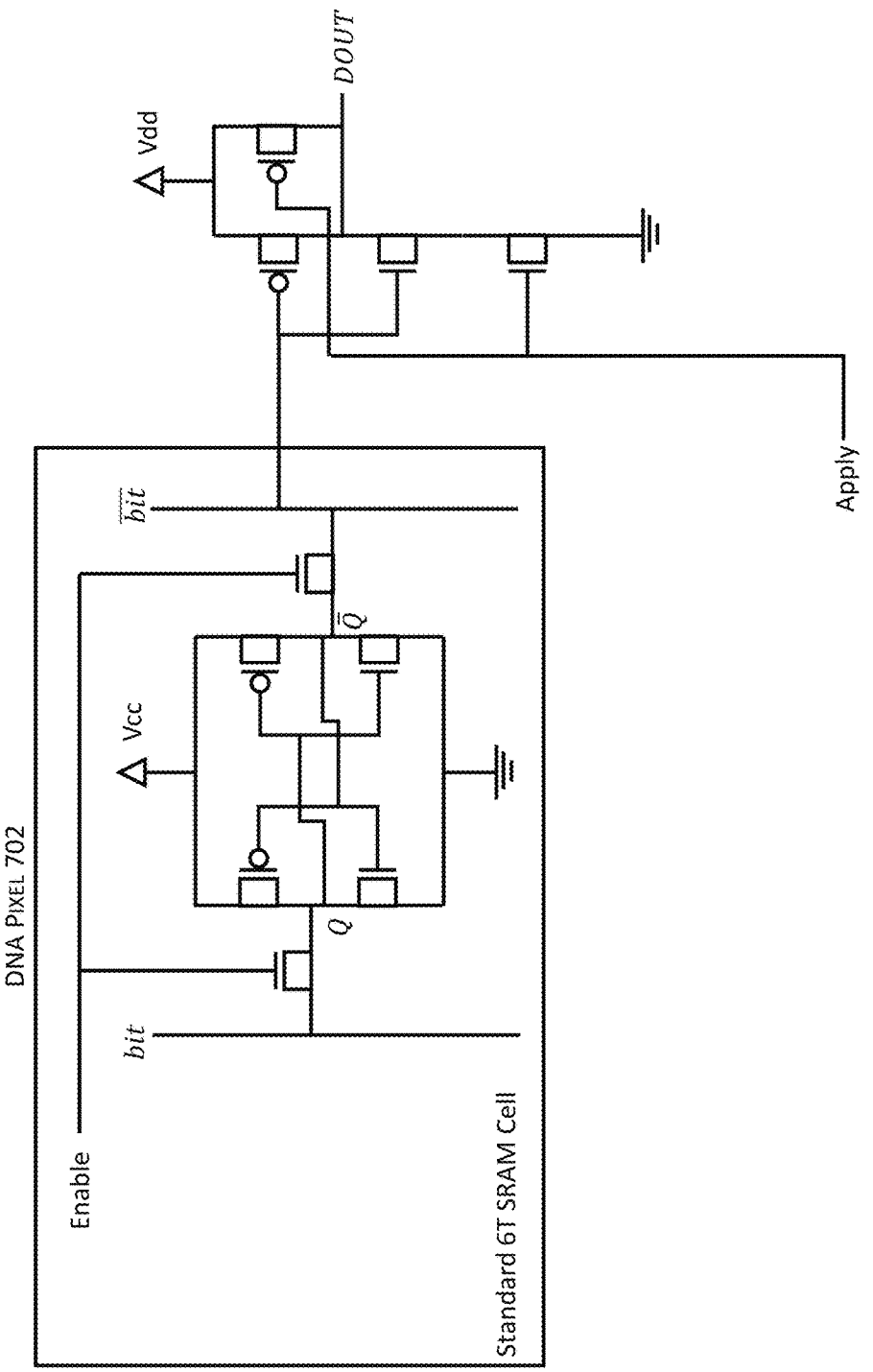
FIG. 8 is a circuitry diagram showing additional details of the circuitry diagram from FIG. 7.

FIG. 8 shows an illustrative circuitry diagram 800 providing additional details of the DNA pixel 702 introduced FIG. 7. In an implementation, the DNA pixel 702 may be implemented as a standard 6T SRAM cell. The standard memory cell may be used as-is or may be optimized to drive a microelectrode array for oligonucleotide synthesis. In some implementations, a sense amplifier (sense AMP) may be omitted. The level shifter may be integrated to drive the appropriate voltage on DOUT.

Illustrative Process

For ease of understanding, the process discussed in this disclosure is delineated as separate operations represented as independent blocks. However, these separately delineated operations should not be construed as a limitation, and unless otherwise contradicted by context any number of the described process blocks may be combined to implement the process or an alternate process. Moreover, it is also possible that one or more of the provided operations is modified or omitted.

Figure 9:
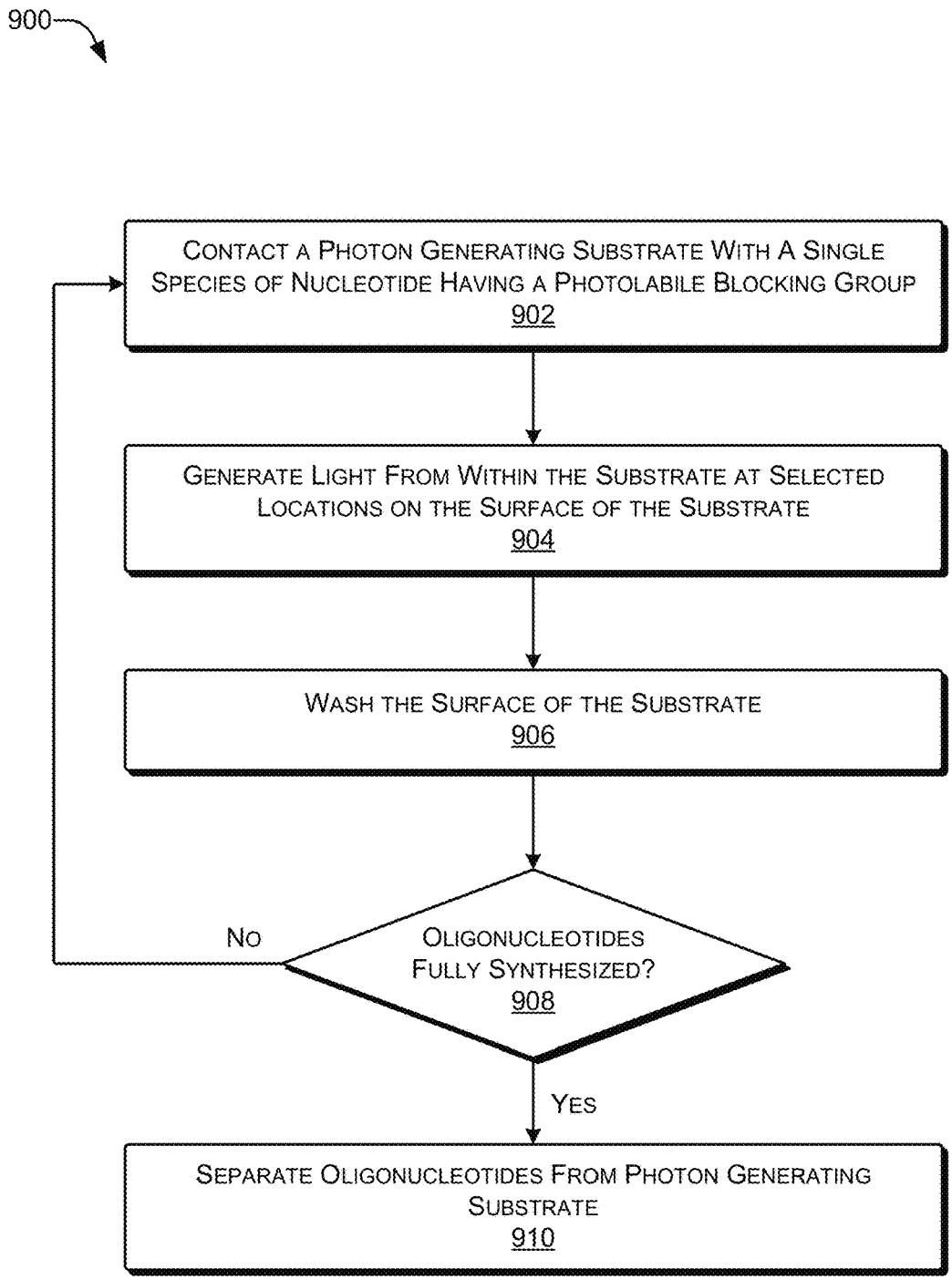
FIG. 9 is a flow diagram showing an illustrative process for de novo synthesis of oligonucleotides using a photon delivery system as described herein.

FIG. 9 shows process 900 for de novo, light-directed synthesis of oligonucleotides using patterned light emitted from within a photon generating substrate. This process 900 may be implemented, for example, using any of the photon delivery systems shown in FIGS. 2-6 or the oligonucleotide synthesizer shown in FIG. 10.

At operation 902, a photon generating substrate is contacted with nucleotides having photolabile blocking groups. The photolabile blocking groups prevent incorporation of more than one nucleotide at a time. A single species of nucleotide or more than once species of nucleotide (e.g., two, three, or four different species) may be flooded in excess over the surface of the photon generating substrate.

For example, the selected nucleotide may be one of deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP). Selection of the nucleotide controls the base sequence of the oligonucleotides that are synthesized on the photon generating substrate during this round of synthesis. Many types of photolabile blocking groups are known to those of ordinary skill in the art and any may be used in process 900. Examples of photolabile blocking groups are provided previously.

At operation 904, patterned light is generated from within the photon generating substrate at selected locations on the surface of the substrate. The photon generating substrate may generate light from within a stack so that patterned light is emitted through an optically transparent top layer on which growing oligonucleotides are anchored. The light is a wavelength that causes separation of at least some of the photolabile blocking groups. The patterned light may create a pattern of illuminated locations on the surface of the photon generating substrate with a pitch size of less than 7 µm, 6 µm, 5 µm, or 4 µm.

The selected location may be any one or more locations that are contiguous or separate on the surface of the photon generating substrate. The selected location may be a single spot, a group of spots located adjacent to each other, or multiple disparate spots spread across the surface of the photon generating substrate in any pattern.

In one implementation, generating patterned light comprises activating individual microLEDs in a microLED array that correspond to the selected locations on the surface of the photon generating substrate. In one implementation, generating patterned light comprises making locations in a liquid crystal panel transparent that correspond to the selected locations on the surface of the photon generating substrate. The liquid crystal panel may be included in a pass-through system in which light from the light source shines through the liquid crystal panel. Alternatively, the liquid crystal panel may be a component of an LCoS system.

At operation 906, the photon generating substrate is washed to remove free nucleotides. The wash solution may be flowed across the entire surface of the photon generating substrate displacing any remaining free nucleotides and any other solution covering the photon generating substrate. This prevents incorporation of an incorrect nucleotide during a subsequent round of synthesis. The wash solution may be an aqueous solution such as water or a buffer. The buffer may be any one of a number of aqueous buffers that are compatible with oligonucleotides.

At operation 908, it is determined if oligonucleotide synthesis is complete. If all oligonucleotides are fully synthesized then synthesis is complete. Process 900 may then proceed along the "yes" path to operation 910. If, however, oligonucleotide synthesis is not yet complete, process 900 proceeds along the "no" path and returns to operation 902 where the oligonucleotides are deblocked at a different selected location on the photon generating substrate. This process may be repeated iteratively during synthesis of a batch of oligonucleotides. During each round of synthesis, the species of nucleotide and the selected location may both be independently varied. This allows for the parallel synthesis of multiple oligonucleotides each with a different sequence.

At operation 910, the oligonucleotides may be separated from the surface of the photon generating substrate. If the oligonucleotides are attached to the substrate by linkers, cleavage of the linkers may release the oligonucleotides. If the linkers are photolabile, light generated from within the photon generating substrate may be used to cleave some or all of the linkers. The wavelength of light used to cleave the photolabile linkers is different than the wavelength of light used to remove the photolabile blocking groups.

Photolabile linkers are cleaved by a specific wavelength of light corresponding to the linker chemistry. There are a large number of known types of photo-cleavable bonds. Common classes of photolabile linkers include nitrobenzyl-based linkers, benzyl nitrile-based linkers, benzyl-based linkers, and carbonyl-based linkers. Amine-to-thiol cross-linkers are also photolabile and may be lengthened by attachment to a polyethylene glycol (PEG) chain.

Amine-to-thiol bonds may be cleaved by ultraviolet (UV) light with a wavelength of about 365-405 nm. The list of functional groups that can be protected include, but are not limited to, phosphates, carboxylates, carbonates, carbamates, thiolates, phenolates, and alkoxides.

One type of photolabile linker uses a UV photo-cleavable C3 spacer arm that includes a nitrobenzene sidechain. Cleavage occurs by irradiation with UV light (300-350 nm). Other examples of photolabile linkers are PC Biotin Phosphoramidite with the formula 1-[2-Nitro-5-(6-(N-(4,4'-dimethoxytrityl))-biotinamidocaproamidomethyl)phenyl]-ethyl-[2-cyanoethyl-(N,N-diisopropyl)]-phosphoramidite, PC Amino-Modifier Phosphoramidite with the formula [(6-Trifluoroacetylamidocaproamidomethyl)-1-(2-nitrophenyl)-ethyl]-2-cyanoethyl-(N,N-diisopropyl)-phosphoramidite, PC Spacer Phosphoramidite with the formula [4-(4,4'-Dimethoxytrityloxy)butyramidomethyl)-1-(2-nitrophenyl)-ethyl]-2-cyanoethyl-(N,N-diisopropyl)-phosphoramidite, and PC Linker Phosphoramidite with the formula 3-(4,4'-Dimethoxytrityl)-1-(2-nitrophenyl)-propan-1-yl-[(2-cyanoethyl)-(N,N-diisopropyl)]-phosphoramiditen (available from Glen Research, Sterling, Va.).

Other techniques for separating polynucleotides from a solid substrate following solid-phase synthesis are known to those of ordinary skill in the art. Any suitable technique may be used. The oligonucleotides may be collected and stored or processed further such as by amplification with polymerase chain reaction (PCR).

Illustrative Device and Computer Architecture

Figure 10:
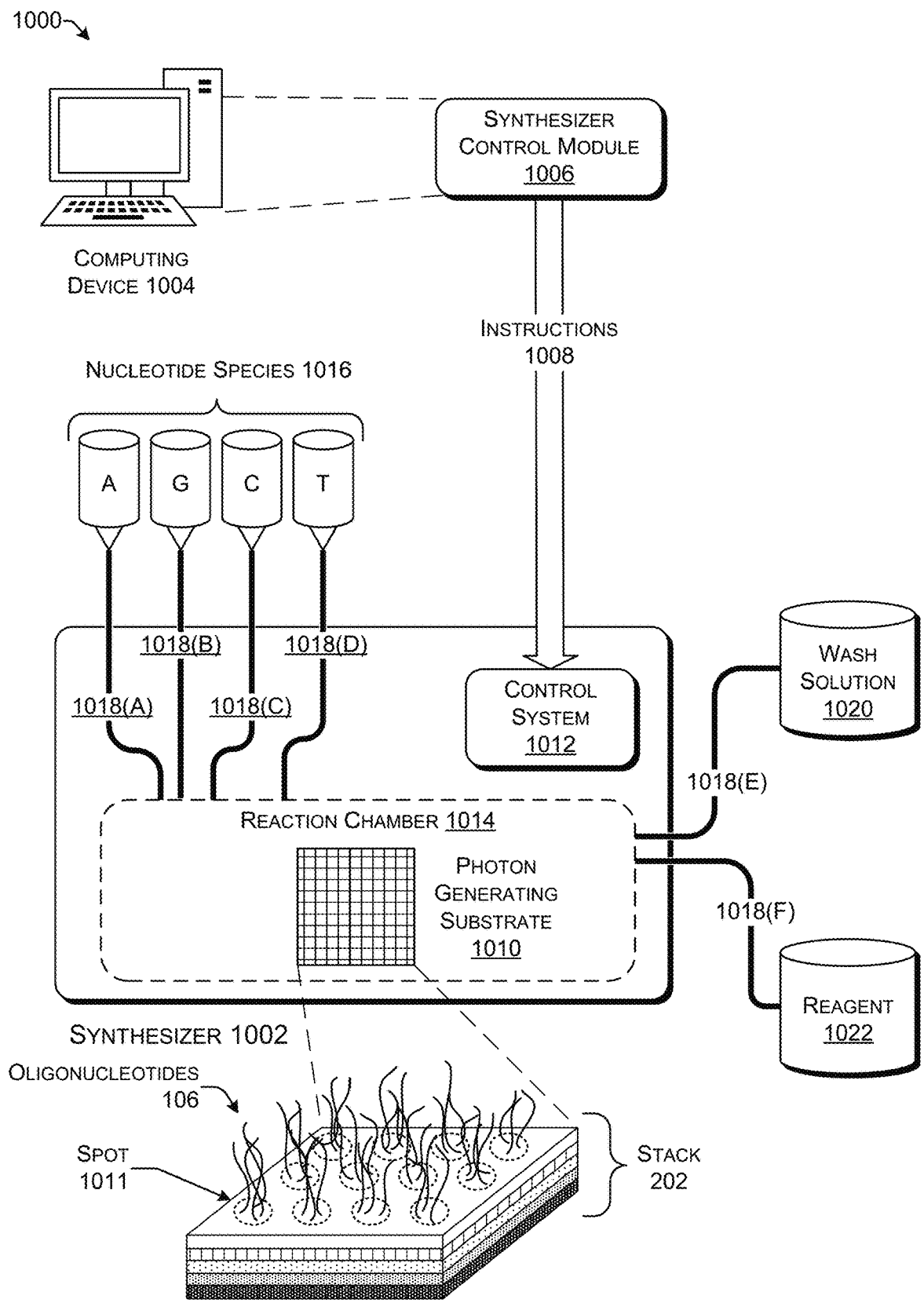
FIG. 10 is an illustrative device for synthesizing oligonucleotides using a photon delivery system as described herein.

FIG. 10 is an illustrative system 1000 for implementing aspects of this disclosure.

The system 1000 includes an oligonucleotide synthesizer 1002 and may also include a computing device 1004. The computing device 1004 includes an oligonucleotide synthesizer control module 1006 that is communicatively connected to the oligonucleotide synthesizer 1002. The oligonucleotide synthesizer control module 1006 provides instructions 1008 that can control operation of the oligonucleotide synthesizer 1002. For example, the instructions 1008 may communicate to the oligonucleotide synthesizer 1002 base sequences of oligonucleotides 106 for synthesis and thereby cause the oligonucleotide synthesizer 1002 to synthesize oligonucleotides 106 with specific sequences and/or that encode specific digital data. The computing device 1004 may be implemented as any type of conventional computing device such as a desktop computer, a laptop computer, a server, a hand-held device, or the like. In an implementation, the computing device 1004 may be a part of the oligonucleotide synthesizer 1002 rather than a separate device.

The oligonucleotide synthesizer 1002 is a device that performs automated solid-phase synthesis of oligonucleotides 106 on a photon generating substrate 1010. The photon generating substrate 1010 may be implemented as a solid-state stack such as any of the stacks shown in FIGS.

2-6. Oligonucleotides 106 may be synthesized on the surface of the stack 202 at discrete spots 1011. All of the oligonucleotides 106 clustered together at a single spot 1011 may have the same sequence. The arrangement, size, and shape of the spots 1011 may be created in part by use of a patterning layer 206 as described previously.

The instructions 1008 may be provided to a control system 1012 configured to provide instructions as electrical signals to a circuitry layer in the stack 202. The instructions from the control system 1012 to the circuitry layer may specify both a timing of activating the light source and the patterning of the light from the light source. The control system 1012 may be implemented as any type of circuitry suitable for controlling hardware devices such as a printed circuit board, microcontroller, a programmable logic controller (PLC), or the like. The control system 1012, by changing the pattern of light can control where oligonucleotide extension occurs on the surface of the photon generating substrate 1010.

The photon generating substrate 1010 may be mounted in a jig and positioned within a reaction chamber reaction 1014 that can contain a solution used for light-directed synthesis of oligonucleotides, such as a reaction reagent solution, in contact with the surface of the photon generating substrate 1010. The reaction chamber 1014 may be positioned above the stack 202 as shown in FIG. 2, 3, 5, or 6 so that fluid is brought into contact with the oligonucleotides 106. In an implementation, the reaction chamber 1014 may be implemented as one or more fluidics channels that pass through the stack 202 such as the fluidics channel 404 shown in FIG. 4.

The oligonucleotide synthesizer 1002 may also include storage tanks, bottles, vials, or other containers or receptacles for storing individual species up nucleotides 1016. A selected one of the nucleotides 1016 may be brought into contact with the photon generating substrate 1010 through a fluid delivery pathway 1018(A). The fluid delivery pathway 1018(A), and all fluid delivery pathways 1018 generally, may be implemented by tubes and pumps, microfluidics, laboratory robotics, or other techniques. The control system 1012 may also control the fluid delivery pathways 1018. Thus, the control system 1012 can control where polymerization occurs through control of the pattern of light and the species of nucleotide that is added during any round of synthesis through control of the fluid delivery pathways 1018.

Microfluidic technology facilitates the automation of chemical and biological protocols. These devices manipulate small quantities of liquid at smaller scales and with higher precision than humans. Digital microfluidic (DMF) technology is one type of flexible microfluidic technology. DMF devices manipulate individual droplets of liquids on a grid of electrodes, taking advantage of a phenomenon called electrowetting on dielectric. Activating electrodes in certain patterns can move, mix, or split droplets anywhere on the chip. Microfluidics also includes full-stack microfluidics which are programmable systems that allow unrestricted combination of computation and fluidics. Examples of microfluidic technology may be found in Willsey et al., *Puddle: A dynamic, error-correcting, full-stack microfluidics platform*, Aplos'19, April 13-17, 183 (2019).

If synthesizing DNA, for example, the nucleotides 1016 may be dNTPs with photolabile blocking groups that include one of the natural bases adenine (A), guanine (G), cytosine (C), or thymine (T). Although four different types of nucleotides 1016 are illustrated in FIG. 10, the oligonucleotide synthesizer 1002 may include fewer types (e.g., omit one of the standard nucleotides) or more types (e.g., include one or more artificial bases). Only one type of selected nucleotide may be provided during each round of synthesis to control which nucleotide is next incorporated into selected ones of the oligonucleotides 106. However, during rounds of synthesis different ones of the available nucleotides 1016 may be introduced to create a plurality of oligonucleotides 106 each with a different nucleotide sequence.

The nucleotides 1016 may be provided in a reaction reagent solution. The reaction reagent solution may be an aqueous solution that contains a selected one of the nucleotides 1016 and at least one of a salt or buffer or an organic solvent. Some examples of suitable buffers are provided in Vincent S. Stoll & John S. Blanchard, *Buffers: Principles and Practice*, 182 Meth. Enzoml., 24 (1990). The reaction reagent solution may also other enzymes, chemicals, etc. known to those of ordinary skill in the art and conventionally used for light-directed oligonucleotide synthesis.

The oligonucleotide synthesizer 1002 may also include a wash solution 1020. The wash solution 1020 may be water (e.g., DI (deionized) water), an aqueous solution that contains at least one of a salt or a buffer, or an organic solvent. The salt or the buffer may be the same as the salt or buffer used in the reaction reagent solution. The wash solution 1020 is flowed into the reaction chamber 1014 through a fluid delivery pathway 1018(E). The wash solution 1020 is used to remove any free nucleotides and other reagents from the reaction chamber 1014. By removal of free nucleotides, the next round of polymerization may occur with a different nucleotide without contamination from the previous round (although multiple rounds of addition of the same nucleotide species are possible).

One or more other reagents 1022 may also be included in the oligonucleotide synthesizer 1002 and brought into contact with the photon generating substrate 1010 though a fluid delivery pathway 1018(F). If multiple other reagents 1022 are available, each may be delivered through a separate fluid delivery pathway 1018(F) or two or more of the other reagents 1022 may share at least in part the same fluid delivery pathway 1018(F). The other reagents 1022 may include, for example, a chemical cleavage agent, a deblocking agent, a redox reagent, a support electrolyte, a metal cofactor, and/or a scavenger.

Figure 11:
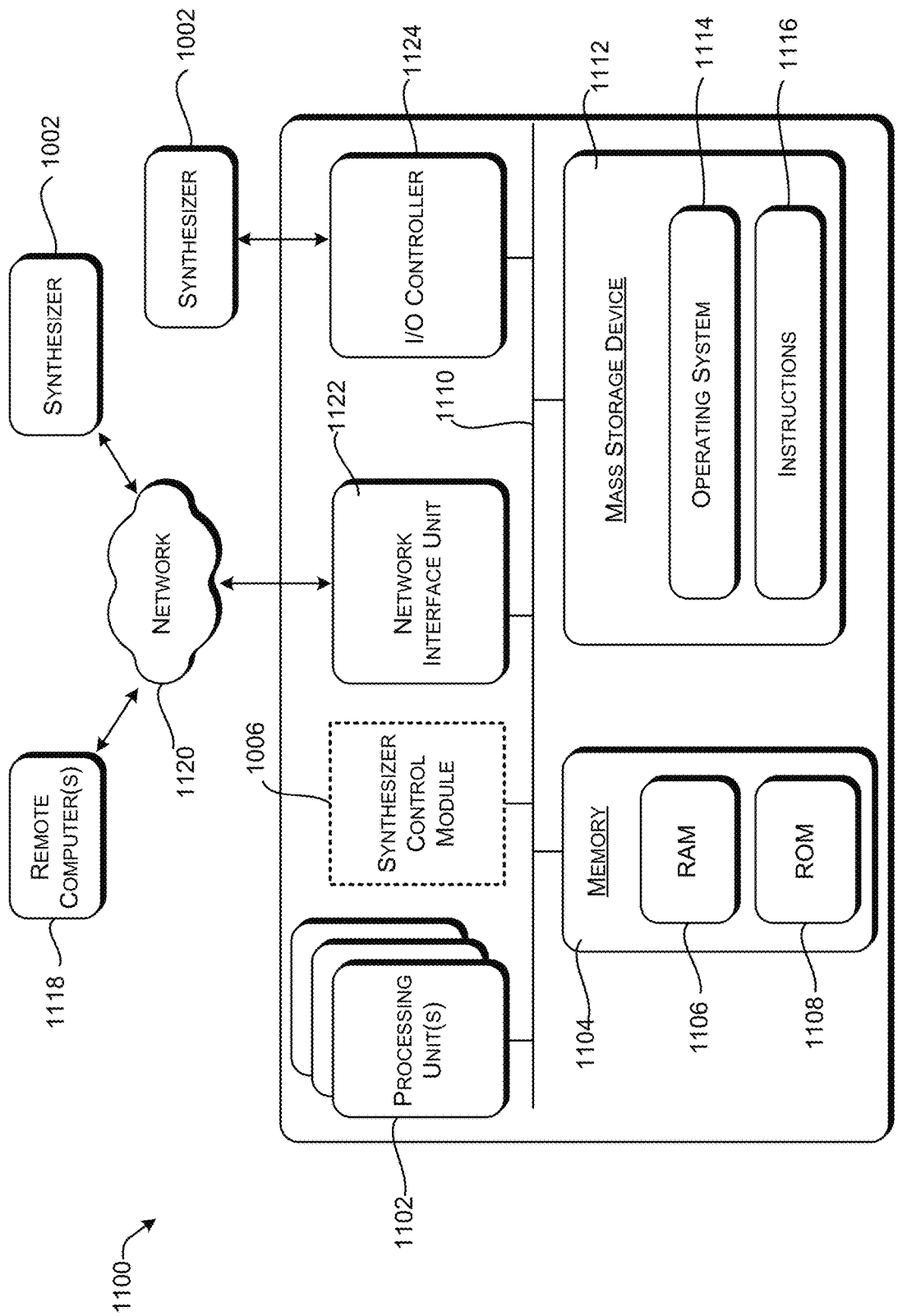
FIG. 11 is an illustrative computer architecture for implementing techniques of this disclosure.

FIG. 11 is a computer architecture diagram showing an illustrative computer hardware and software architecture for a computing device such as the computing device 1004 introduced FIG. 10. In particular, the computer 1100 illustrated in FIG. 11 can be utilized to implement the oligonucleotide synthesizer control module 1006.

The computer 1100 includes one or more processing units 1102, a memory 1104, that may include a random-access memory 1106 ("RAM") and a read-only memory ("ROM") 1108, and a system bus 1110 that couples the memory 1104 to the processing unit(s) 1102. A basic input/output system ("BIOS" or "firmware") containing the basic routines that help to transfer information between elements within the computer 1100, such as during startup, can be stored in the ROM 1108. The computer 1100 further includes a mass storage device 1112 for storing an operating system 1114 and other instructions 1116 that represent application programs and/or other types of programs such as, for example, instructions to implement the oligonucleotide synthesizer control module 1006. The mass storage device 1112 can also be configured to store files, documents, and data such as, for example, sequence data that is provided to the oligonucleotide synthesizer 1002 in the form of instructions 1008.

The mass storage device 1112 is connected to the processing unit(s) 1102 through a mass storage controller (not shown) connected to the bus 1110. The mass storage device 1112 and its associated computer-readable media provide non-volatile storage for the computer 1100. Although the description of computer-readable media contained herein refers to a mass storage device, such as a hard disk, solid-state drive, CD-ROM drive, DVD-ROM drive, or USB storage key, it should be appreciated by those skilled in the art that computer-readable media can be any available computer-readable storage media or communication media that can be accessed by the computer 1100.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared, and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules or other data. For example, computer-readable storage media includes, but is not limited to, RAM 1106, ROM 1108, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 1100. For purposes of the claims, the phrase "computer-readable storage medium," and variations thereof, does not include waves or signals per se or communication media.

According to various configurations, the computer 1100 can operate in a networked environment using logical connections to a remote computer(s) 1118 through a network 1120. The computer 1100 can connect to the network 1120 through a network interface unit 1122 connected to the bus 1110. It should be appreciated that the network interface unit 1122 can also be utilized to connect to other types of networks and remote computer systems. The computer 1100 can also include an input/output (I/O) controller 1124 for receiving and processing input from a number of other devices, including a keyboard, mouse, touch input, an electronic stylus (not shown), or equipment such as a oligonucleotide synthesizer 1002 for synthesizing oligonucleotide according to the techniques of this disclosure. Similarly, the input/output controller 1124 can provide output to a display screen or other type of output device (not shown).

It should be appreciated that the software components described herein, when loaded into the processing unit(s) 1102 and executed, can transform the processing unit(s) 1102 and the overall computer 1100 from a general-purpose computing device into a special-purpose computing device customized to facilitate the functionality presented herein. The processing unit(s) 1102 can be constructed from any number of transistors or other discrete circuit elements, which can individually or collectively assume any number of states. More specifically, the processing unit(s) 1102 can operate as a finite-state machine, in response to executable instructions contained within the software modules disclosed herein. These computer-executable instructions can transform the processing unit(s) 1102 by specifying how the processing unit(s) 1102 transitions between states, thereby transforming the transistors or other discrete hardware elements constituting the processing unit(s) 1102.

Encoding the software modules presented herein can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 1100 to store and execute the software components presented herein. It also should be appreciated that the architecture shown in FIG. 11 for the computer 1100, or a similar architecture, can be utilized to implement many types of computing devices such as desktop computers, notebook computers, servers, supercomputers, gaming devices, tablet computers, and other types of computing devices known to those skilled in the art. For example, the computer 1100 may be wholly or partially integrated into the oligonucleotide synthesizer 1002. It is also contemplated that the computer 1100 might not include all of the components shown in FIG. 11, can include other components that are not explicitly shown in FIG. 11, or can utilize an architecture different than that shown in FIG. 11.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A photon delivery system comprising: a solid-state stack (202) comprising: a solid substrate (102, 204, 402) coated with a plurality of oligonucleotides (106); a light source (108) configured to emit a pattern of light at a specified wavelength; and a circuitry layer (212) configured to control the pattern of light emitted from the light source (108) and incident upon the solid substrate (102, 204, 402).

Clause 2. The photon delivery system of clause 1, wherein the light source comprises a microLED array.

Clause 3. The photon delivery system of clause 2, wherein the microLED array comprises gallium nitride (GaN) LEDs that emit light at a wavelength of about 365 nm.

Clause 4. The photon delivery system of clause 2, wherein the microLED array comprises an integrated memory cell for each microLED in the microLED array.

Clause 5. The photon delivery system of clause 1, wherein the light source comprises a lamp, a laser, an LED, or a microLED, and the photon delivery system further comprises a pass-through liquid crystal panel.

Clause 6. The photon delivery system of clause 1, wherein the light source comprises a lamp, a laser, an LED, or a microLED, and the photon delivery system further comprises an LCoS system.

Clause 7. The photon delivery system of any of clauses 1-6, further comprising a fluidics channel and wherein the fluidics channel is located between the solid substrate coated with the plurality of oligonucleotides and the light source.

Clause 8. The photon delivery system of any of clauses 1-7, wherein the solid substrate is a transmissive layer comprising silicon dioxide glass or quartz.

Clause 9. The photon delivery system of any of clauses 1-8, wherein the solid substrate is silanized.

Clause 10. The photon delivery system of any of clauses 1-9, further comprising a patterning layer that prevent passage of light from the light source through to the plurality of oligonucleotides.

Clause 11. The photon delivery system of any of clauses 1-9, further comprising a patterning layer that limits attachment of oligonucleotides to only discrete spots on the solid substrate.

Clause 12. The photon delivery system of any of clauses 1-11, further comprising a focusing layer configured to direct light from the light source onto the solid substrate.

Clause 13. The photon delivery system of clause 12, wherein the focusing layer comprises a collimator.

Clause 14. The photon delivery system of clause 13, wherein the collimator comprises collimating microlenses positioned between individual microLEDs in a microLED array and the solid substrate.

Clause 15. The photon delivery system of clauses 1-14, further comprising a control system configured to provide instructions to the circuitry layer that specify both a timing of activating the light source and the pattern of light emitted from the light source.

Clause 16. A method for light-directed synthesis of oligonucleotides, the method comprising: a) contacting a photon generating substrate with a single species of nucleotide having a photolabile blocking group; b) generating patterned light from within the photon generating substrate at a wavelength that causes separation of the photolabile blocking group, the patterned light generated at selected locations on a surface of the photon generating substrate; c) washing the surface of the photon generating substrate; and d) repeating steps a-c until a plurality of oligonucleotides with different sequences are fully synthesized.

Clause 17. The method of clause 17, wherein during iterations of repeating steps a-c the selected locations or the single species of nucleotide change at least once.

Clause 18. The method of any of clauses 16-17, wherein generating patterned light comprises activating individual microLEDs in a microLED array that correspond to the selected locations on a surface of the photon generating substrate.

Clause 19. The method of any of clauses 16-17, wherein generating patterned light comprises making locations in a liquid crystal panel transparent that correspond to the selected locations on a surface of the photon generating substrate.

Clause 20. The method of any of clauses 16-19, wherein generating patterned light comprises generating a pattern of illuminated locations on a surface of the photon generating substrate with a pitch size of 5 μm or less.

Conclusion

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents, and/or patent applications throughout this specification. Each of the cited references is individually incorporated herein by reference for its particular cited teachings as well as for all that it discloses.

The invention claimed is:

1. An oligonucleotide synthesis system comprising:
   an oligonucleotide synthesizer, configured to perform automated solid-phase synthesis of oligonucleotides and store individual species of nucleotides, the oligonucleotide synthesizer comprising;
   a photon generating substrate;
   a reaction chamber; and
   a solid-state stack comprising:
      an optically transparent, solid substrate coated with a plurality of oligonucleotides;
      a light source configured to emit a pattern of light at a specified wavelength;
      a focusing layer, separate from and adjacent to the solid substrate, configured to direct light from the light source onto the solid substrate, wherein the focusing layer comprises an array of collimating microlenses; and
      a circuitry layer configured to control the pattern of light emitted from the light source and incident upon the solid substrate; and
   a computing device comprising an oligonucleotide synthesizer control module, connected to the oligonucleotide synthesizer, wherein the oligonucleotide control module is configured to cause the oligonucleotide synthesizer to synthesize the oligonucleotides.

2. The oligonucleotide synthesis system of claim 1, wherein the light source comprises a microLED array.

3. The oligonucleotide synthesis system of claim 2, wherein the microLED array comprises gallium nitride (GaN) LEDs that emit light at a wavelength of about 365 nm.

4. The oligonucleotide synthesis system of claim 2, wherein the microLED array comprises an integrated memory cell for each microLED in the microLED array.

5. The oligonucleotide synthesis system of claim 1, wherein the light source comprises a lamp, a laser, an LED, or a microLED, and further comprises a pass-through liquid crystal panel.

6. The oligonucleotide synthesis system of claim 1, wherein the light source comprises a lamp, a laser, an LED, or a microLED, and further comprises an LCoS system.

7. The oligonucleotide synthesis system of claim 1, further comprising a fluidics channel and wherein the fluidics channel is located between the solid substrate coated with the plurality of oligonucleotides and the light source.

8. The oligonucleotide synthesis system of claim 1, wherein the solid substrate is a transmissive layer comprising silicon dioxide glass or quartz.

9. The oligonucleotide synthesis system of claim 1, wherein the solid substrate is silanized.

10. The oligonucleotide synthesis system of claim 1, further comprising a patterning layer that prevents passage of light from the light source through to the plurality of oligonucleotides.

11. The oligonucleotide synthesis system of claim 1, further comprising a patterning layer that limits attachment of oligonucleotides to only discrete spots on the solid substrate.

12. The oligonucleotide synthesis system of claim 1, wherein the collimating microlenses are positioned between individual microLEDs in a microLED array and the solid substrate.

13. The oligonucleotide synthesis system of claim 1, wherein the oligonucleotide synthesizer control module is configured to provide instructions to the circuitry layer that specify both a timing of activating the light source and the pattern of light emitted from the light source.

14. The oligonucleotide synthesis system of claim 1, wherein the oligonucleotides encode digital data.

15. The oligonucleotide synthesis system comprising:
   an oligonucleotide synthesizer, configured to perform automated solid-phase synthesis of oligonucleotides and store individual species of nucleotides, the oligonucleotide synthesizer comprising;
   a photon generating substrate;
   a reaction chamber; and
   a solid-state stack comprising:
      a substrate;
      a circuitry layer, over the substrate, configured to control light emitted from a light source;
      the light source, over the circuitry layer, wherein the light source is a microLED array configured to emit a pattern of light at a specified wavelength;
      a focusing layer, over the light source, configured to direct light from the light source onto a transmissive layer, wherein the focusing layer comprises an array of collimating microlenses each aligned with a corresponding one of the microLEDs in the microLED array;
      the transmissive layer, separate from and disposed over the focusing layer, formed of an optically transparent material which is a solid substrate configured to be coated with a plurality of oligonucleotides,
      wherein the oligonucleotides exclusively attach to functionalized regions on the surface of the transmissive layer; and
      a patterning layer configured to limit locations for attachment of the oligonucleotides to the transmissive layer; and
   a computing device comprising an oligonucleotide synthesizer control module, connected to the oligonucleotide synthesizer, wherein the oligonucleotide control module is configured to cause the oligonucleotide synthesizer to synthesize the oligonucleotides.

16. The oligonucleotide synthesis system of claim 15, wherein the substrate is a printed circuit board (PCB) or a bare wafer.

17. The oligonucleotide synthesis system of claim 15, wherein the circuitry layer comprises a hybrid CMOS and integrated circuit (IC) hybrid assembly configured to drive the microLED array.

18. The oligonucleotide synthesis system of claim 15, wherein a pattern of the patterning layer is formed by micro-etching that creates topographical structures or by overlaying non-transparent material.

19. The oligonucleotide synthesis system of claim 15, wherein the patterning layer is further configured to limit transmission of light.

20. The oligonucleotide synthesis system of claim 15, wherein the oligonucleotides encode digital data.

* * * * *